(12) United States Patent
Chi et al.

(10) Patent No.: US 9,623,349 B2
(45) Date of Patent: Apr. 18, 2017

(54) DISPOSABLE INTEGRATED POLYMERIC VACUUM FILTRATION FUNNEL

(71) Applicants: Haitao Chi, Zhejing Province (CN); Haifeng Zhu, Sugar Land, TX (US); Yawu Thomas Chi, Sugar Land, TX (US)

(72) Inventors: Haitao Chi, Zhejing Province (CN); Haifeng Zhu, Sugar Land, TX (US); Yawu Thomas Chi, Sugar Land, TX (US)

( * ) Notice: Subject to any disclaimer, the term of this patent is extended or adjusted under 35 U.S.C. 154(b) by 0 days.

(21) Appl. No.: 14/221,953

(22) Filed: Mar. 21, 2014

(65) Prior Publication Data
US 2014/0291234 A1    Oct. 2, 2014

(30) Foreign Application Priority Data
Mar. 25, 2013   (CN) .......................... 2013 1 0098213

(51) Int. Cl.
*B01D 29/085*   (2006.01)
*B01L 3/00*   (2006.01)
*G01N 1/40*   (2006.01)

(52) U.S. Cl.
CPC .............. *B01D 29/085* (2013.01); *B01L 3/56* (2013.01); *B01L 3/502* (2013.01); *B01L 2300/0681* (2013.01); *G01N 2001/4088* (2013.01)

(58) Field of Classification Search
CPC .. B01L 27/146; B01L 3/56; B01L 2300/0681; B01D 23/28
See application file for complete search history.

(56) References Cited

U.S. PATENT DOCUMENTS 3,782,175 A * 1/1974 Roman .................. 73/61.41
3,971,721 A * 7/1976 Fogarty, Jr. ............ 210/401
(Continued)

FOREIGN PATENT DOCUMENTS

EP    0321064 A1    6/1989

OTHER PUBLICATIONS

Florida Seal & Rubber, Custom Molded Rubber Seals, Aug. 23, 2011.   http://www.flaseal.com/sealing-solutions/custom-molded-seals.aspx (Archival copy obtained with WayBack Machine https://web.archive.org/web/20110823202448/http://www.flaseal.com/sealing-solutions/custom-molded-seals.aspx).*

(Continued)

*Primary Examiner* — Jill Warden
*Assistant Examiner* — Matthew Krcha
(74) *Attorney, Agent, or Firm* — Steven N. Fox, Esq.

(57) ABSTRACT

This invention discloses a disposable integrated polymeric vacuum filtration funnel. The integrated polymeric vacuum filtration funnel comprises a filtration funnel body having a filter frit disposed inside at the bottom, an outlet stem connected with an outlet at the outer bottom of the filtration funnel body; the outlet stem is integrated with the filtration funnel body; the filter frit is sealed to the inner bottom and the inner side surface of the filtration funnel body; the integrated polymeric vacuum filtration funnel comprises a sealing joint disposed underneath the outer bottom of the filtration funnel body, the sealing joint having a side-arm for vacuum connection and a standard adaptor to connect the receiving receptacle; the outlet stem protrudes from the standard adaptor; the filter frit, filtration funnel body, and sealing joint are integrated as one device. The invention can effectively reduce or eliminate the loss of the filtrate and filter cake, avoid contamination, easy to use, and cost-effective.

17 Claims, 15 Drawing Sheets

(56) References Cited

U.S. PATENT DOCUMENTS

| | | | |
|---|---|---|---|
| 4,357,240 A | 11/1982 | Mehra et al. | |
| 6,443,314 B2* | 9/2002 | Shiraiwa et al. | 210/474 |
| 2003/0080045 A1* | 5/2003 | Zuk, Jr. | 210/416.1 |
| 2010/0038303 A1* | 2/2010 | Cai et al. | 210/406 |

OTHER PUBLICATIONS

Examination Report dated Sep. 3, 2014, issued by the State Intellectual Property Office of The People's Republic of China in corresponding Chinese Patent Application No. CN-201310098213.8, with English machine-translation (12 pages).

* cited by examiner

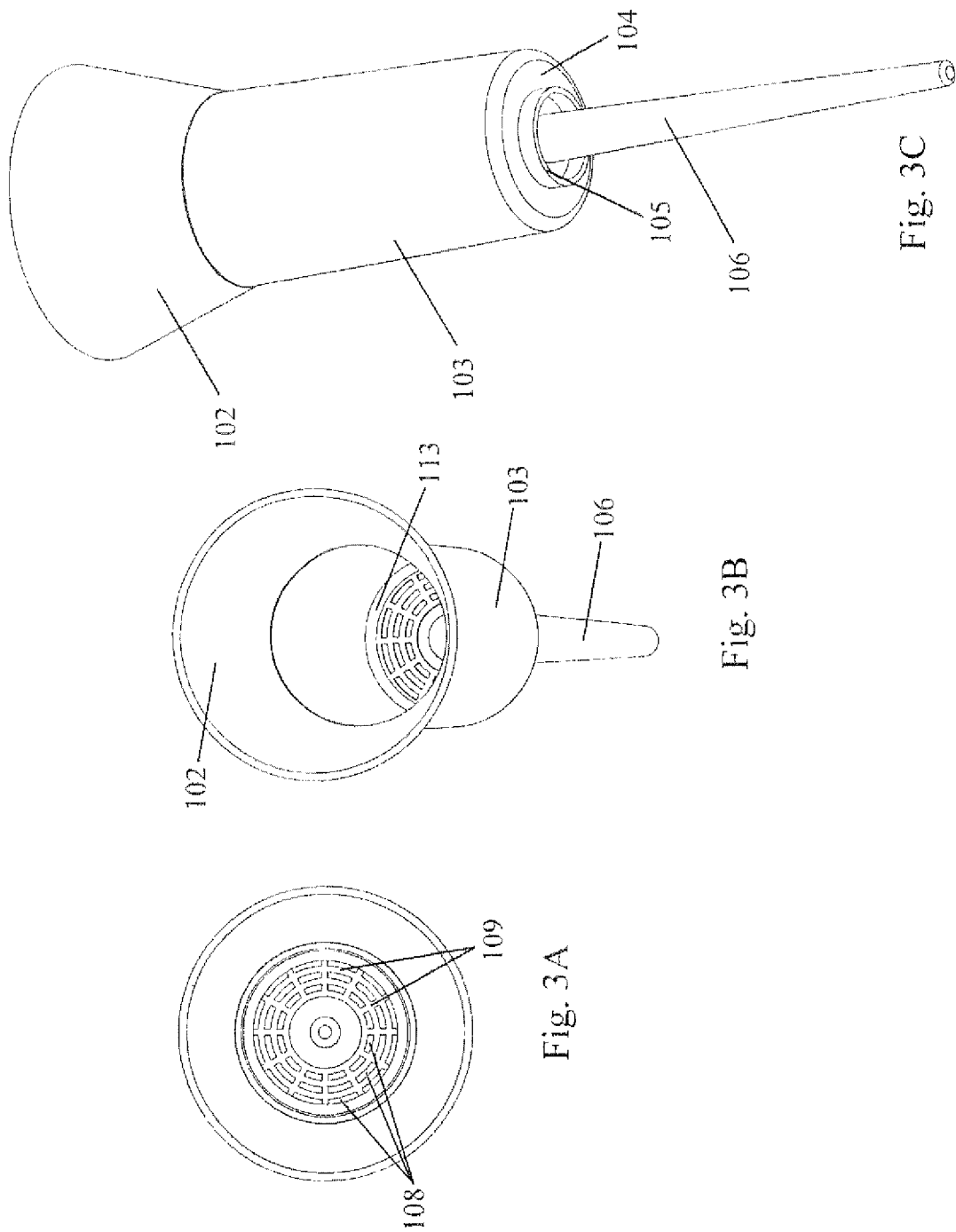

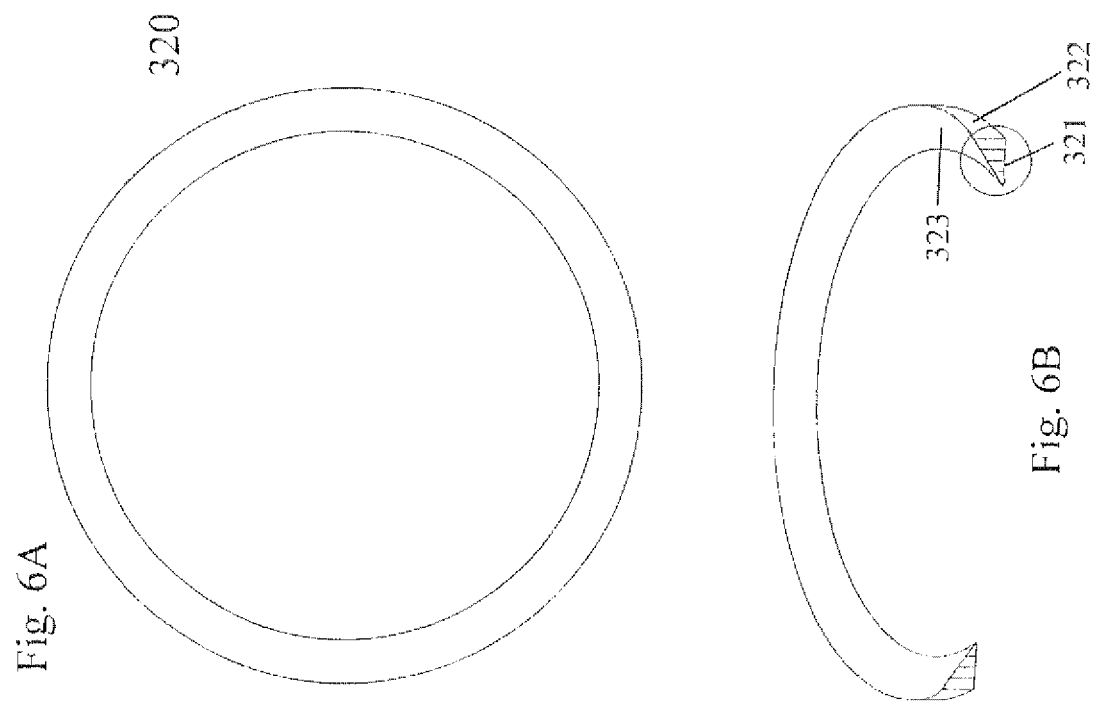

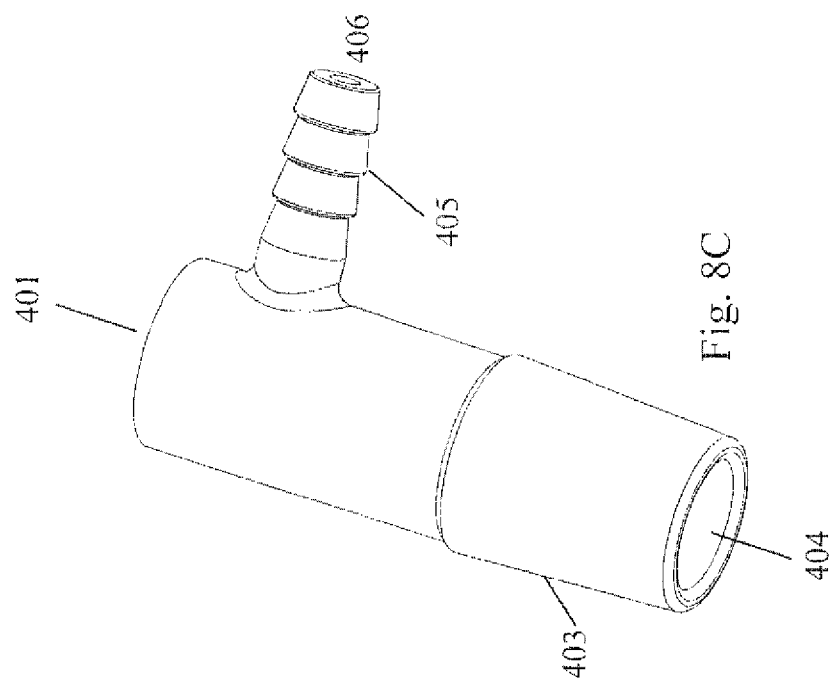
Fig. 8C
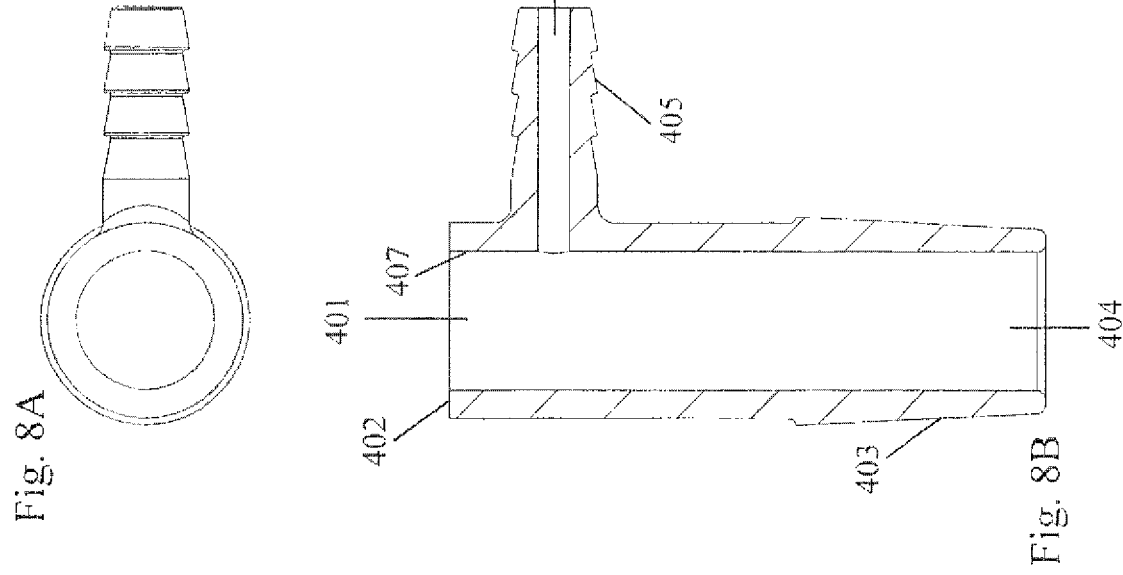
Fig. 8A
Fig. 8B

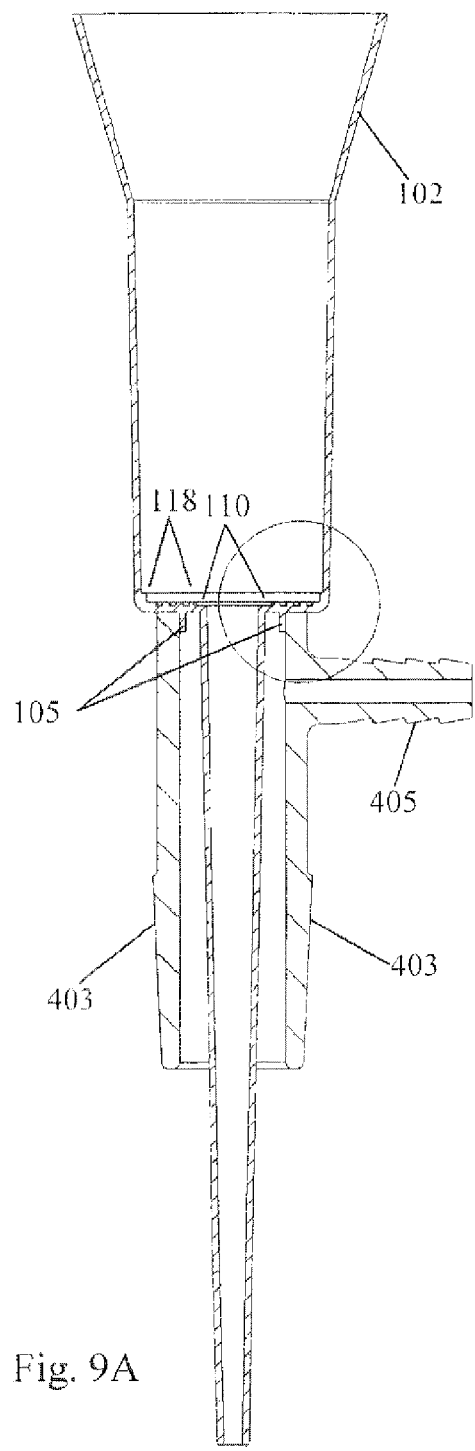
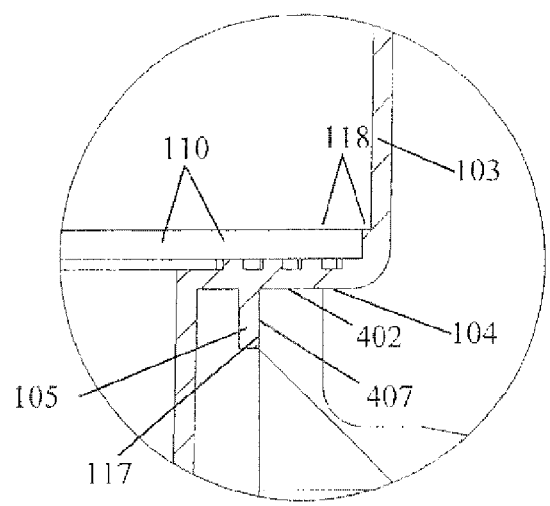
Fig. 9A
Fig. 9B

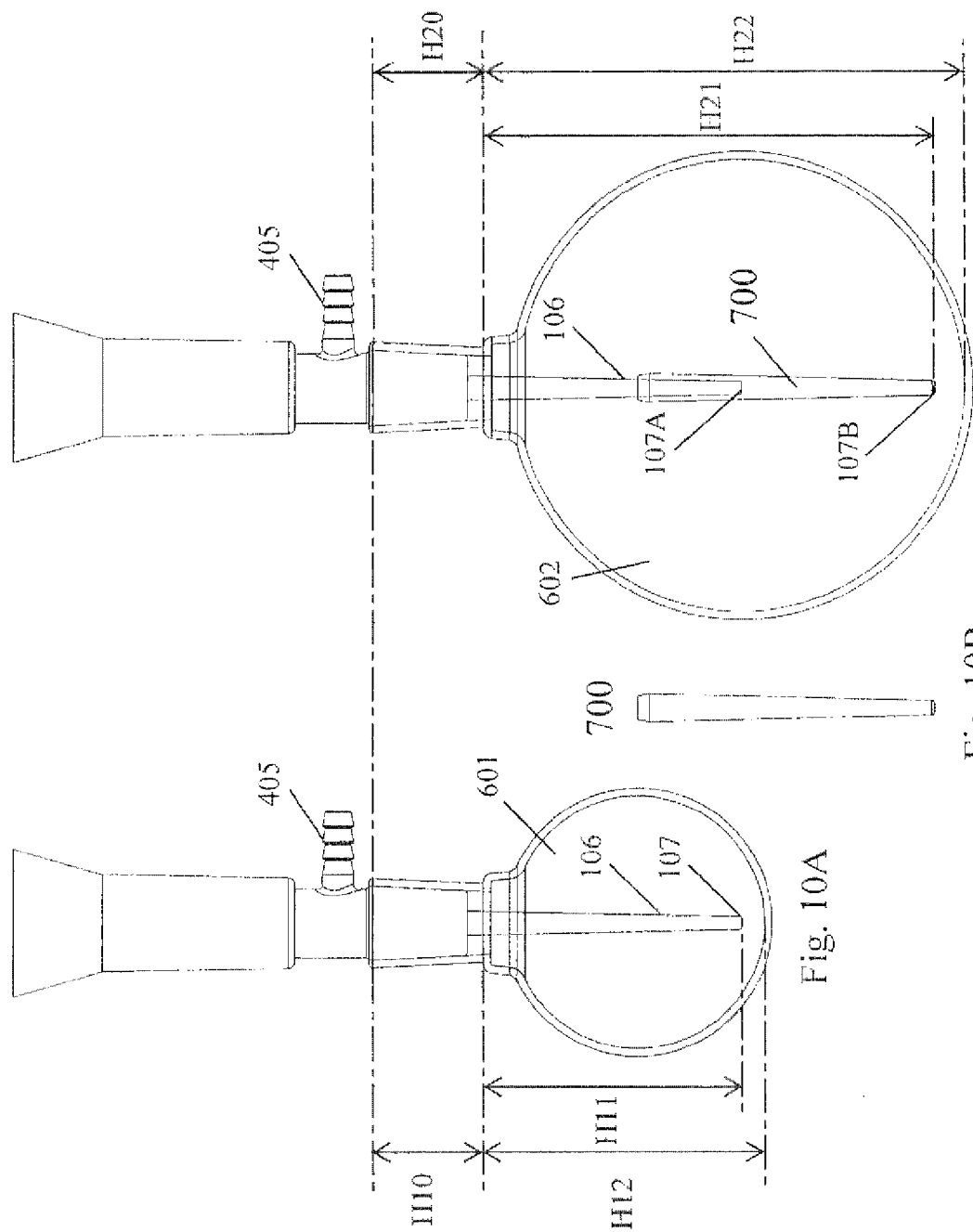

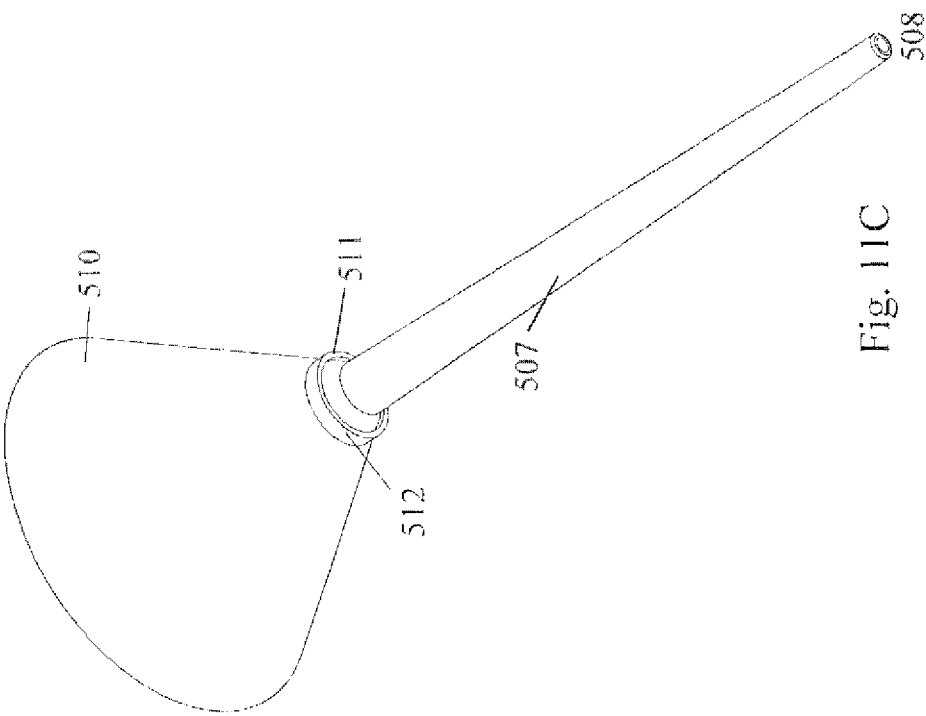
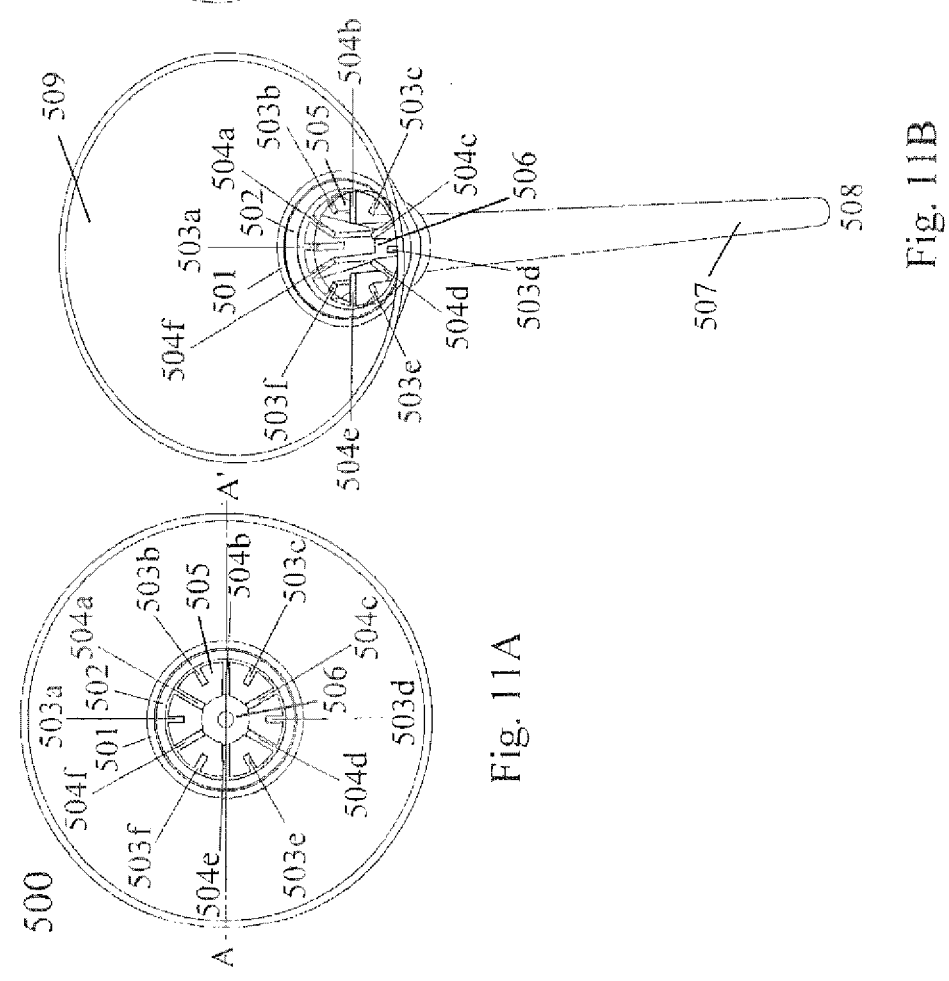
Fig. 11A  Fig. 11B  Fig. 11C

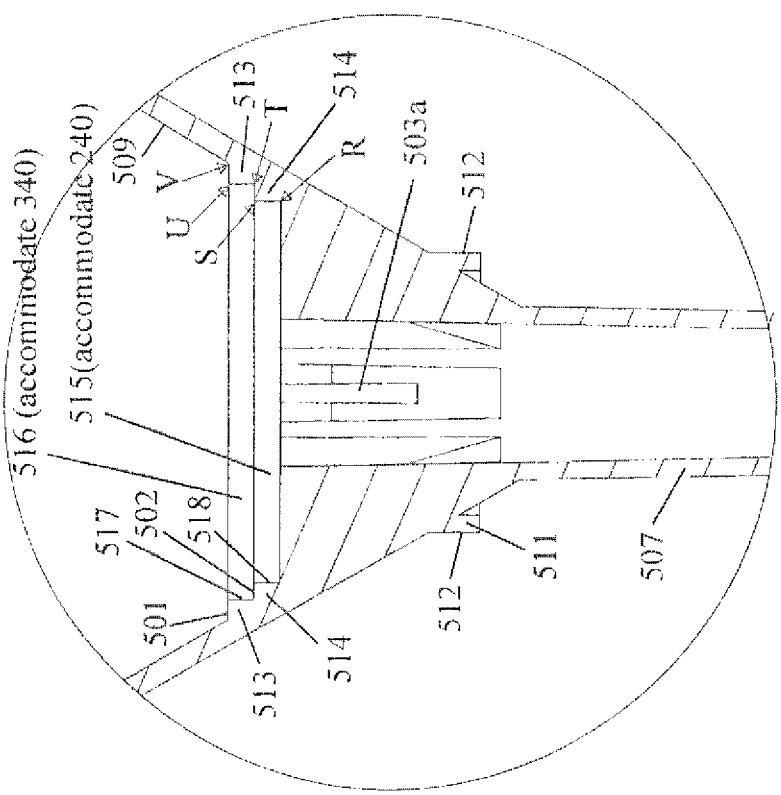
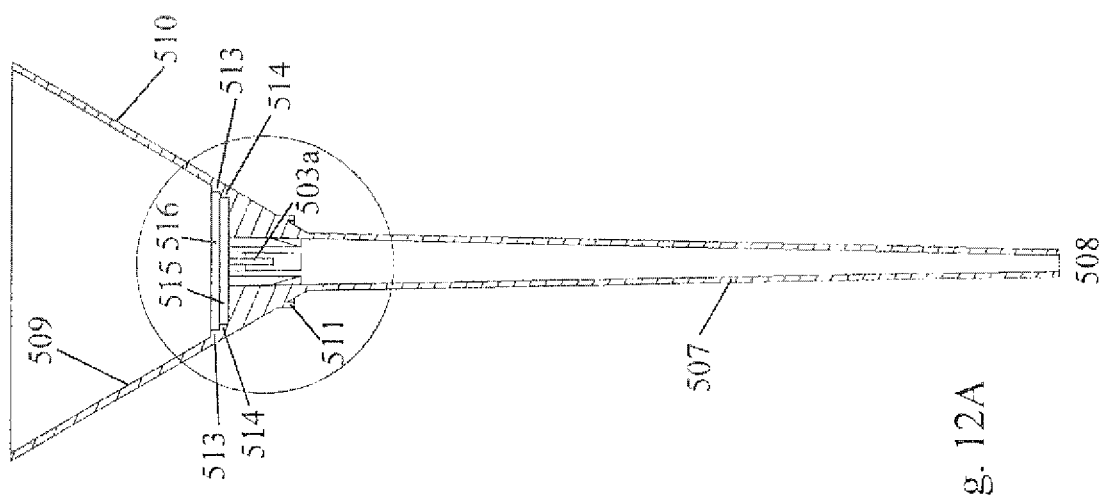
Fig. 12B
Fig. 12A

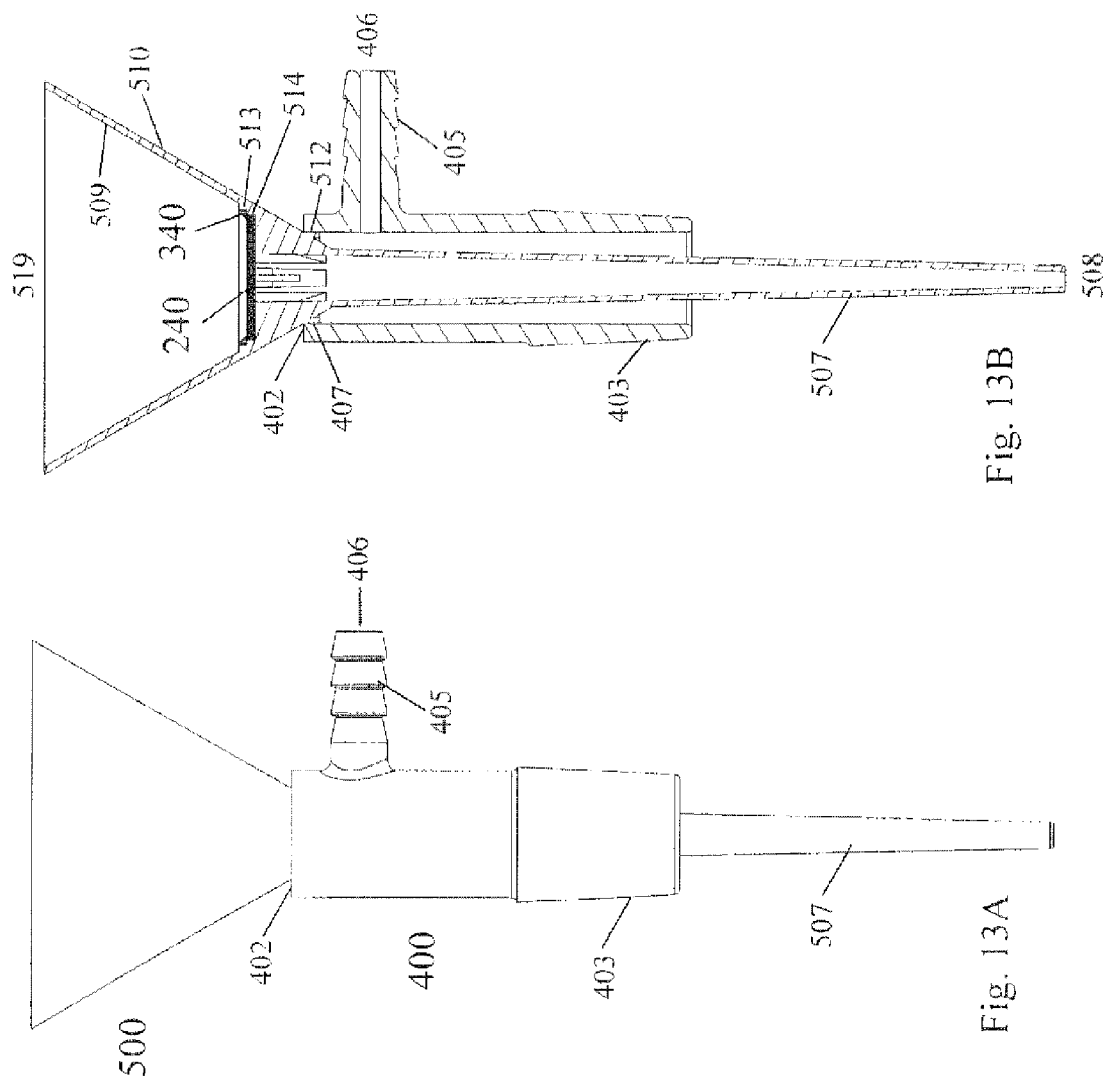

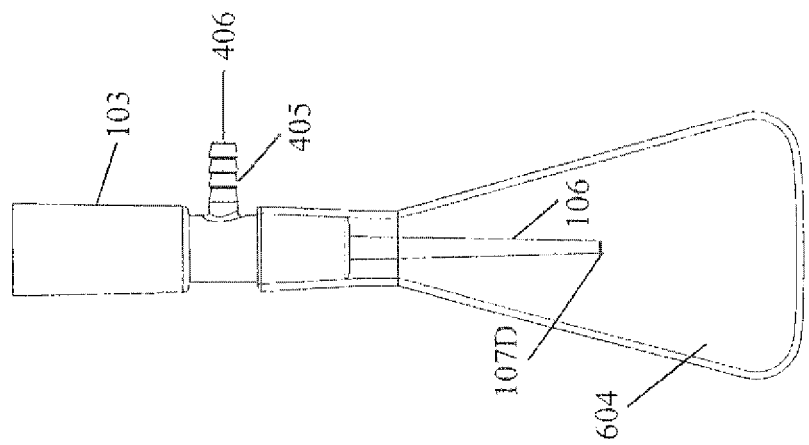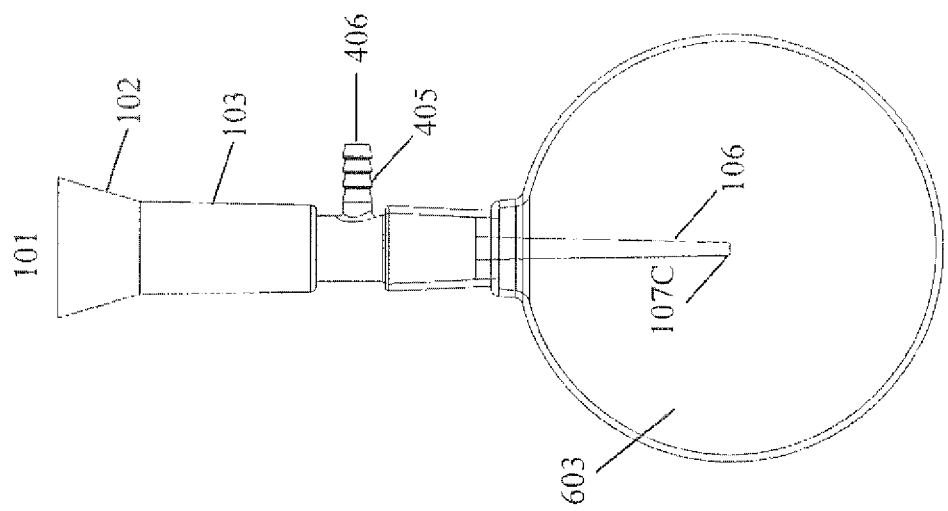
Fig. 14B
Fig. 14A

DISPOSABLE INTEGRATED POLYMERIC VACUUM FILTRATION FUNNEL

TECHNOLOGY FIELD

This invention relates to the field of solid-liquid filtration and separation, particularly to a disposable integrated polymeric vacuum filtration funnel, mainly used in the solid-liquid filtration and separation under the vacuum conditions.

BACKGROUND OF THE INVENTION

Filtration is one of the separation means commonly used in the laboratory to separate the solid particles out of the solid-liquid mixture. When the solid-liquid mixture is brought in contact with a filter media surface, the liquid passes through the filter media, but the solid material retains on the filter. Vacuum filtration is one of the rapid filtration methods commonly used in laboratory. The vacuum filtration involves a vacuum suction to cause pressure gradient which draws the fluid through the filter media such as filter paper, allowing for higher filtration rates and faster filtering than gravity filtration. The vacuum filtration devices usually consist of a filtration funnel, a side-arm connecting to a vacuum source, and a receiving receptacle. Sometimes, an adaptor may be needed to connect the filtration funnel and the receiving receptacle.

Buchner funnels as commonly used vacuum filtration devices are widely used. Some Buchner funnels come with side-arm connecting to the vacuum source, some do not. Buchner funnel without side-arm usually requires the use of neoprene or silicone rubber seal or frit to connect the receiving receptacle, such as flasks. In the operation of the vacuum filtration, the wear debris generated from the rubber seal can enter into the receiving receptacle, causing serious contaminations to the filtered fluid sample. After continued use, the rubber seals gradually wear or dry out, eventually leading to an air leak into the filtration system and resultant reduction in the vacuum filtration speed and effectiveness.

Buchner funnels are mainly made of porcelain and glass. It is very difficult to clean the perforated plate and/or filter media of Buchner funnels due to the clogging or obstruction by solid materials. The clogging solid materials may eventually enter into the receiving receptacle, easily contaminating the filtered samples. The clogging solid materials, such as catalyst particles, may also directly or indirectly react with the filtered samples, significantly impacting the purity and/or quality of the filtered samples. Sometimes the solid materials are the target product to be collected in some filtrations. For example, the precipitated solid materials are usually the target product to be collected in the material synthesis. In the application of the Buchner funnels with fritted filter discs made of borosilicate, quartz, or other porous materials, the pores of the filter media become easily clogged up by solid materials. The fritted filter disc must be thoroughly washed with a variety of solvents in multi-steps and unclogged prior to reuse. For example, to remove aluminous and siliceous residues inside the clogged pores, a recommended cleaning solution is 2% hydrofluoric acid followed by concentrated sulfuric acid; rinse immediately with distilled water followed by a few milliliters of acetone, and repeat the rinsing until all traces of acid are removed. To avoid irritating and corrosive hydrofluoric acid and concentrated sulfuric acid spills and burns, eye protection and chemically resistant gloves should be used when washing the Buchner funnels with fritted discs. An apron and fume hood may also be required depending on the cleaning solutions being used. Meanwhile, the use of significant amount of water and cleaning solvent will increase the filtration cost and effort.

Both 100 mL round bottom flask and 100 mL flat bottom flask with 24/40 standard taper joints are two types of the most commonly used flasks in the chemistry laboratory. The flask body depths (the distance from the bottom of the outer ground joint to the bottom of the flask) of above two types of flasks are both about 80 mm. The flask body depth may vary with the flask volume to some extent. For example, the flask body depths of, another commonly used, 250 mL short neck round bottom flask and flat bottom flask with 24/40 standard taper joint are about 100 mm and 95 mm, respectively. Similarly, the flask body depths of, further another commonly used, 50 mL round bottom flask and flat bottom flask with 24/40 standard taper joint are both about 58 mm. As compared to above flasks, 1000 mL round bottom flask and flat bottom flask with 24/40 standard taper joint are relatively not commonly used and their flask body depths are about 149 mm and 145 mm, respectively.

Currently, all the filtration funnels or Buchner funnels with side-arms are made of glass and have short outlet stems. The outlet tip of the short stem is not far away from the side-arm close to the vacuum source, and also barely or slightly protrudes the bottom of the connection joint. Therefore, as compared to the body depths of above commonly used 250 mL, 100 mL, and 125 mL flasks, the outlet tip the short stem of the Buchner funnels is observably in the upper part of receiving flask. In filtration operation, sometimes the liquid or filtered fluid is the target product to be collected. The existing design of the short outlet stem and the location of the outlet tip close to the side-arm connecting to the vacuum source will significantly increase the loss of volatile samples under vacuum filtration and the loss of filtered fluid samples sucked into the vacuum source. In some cases involving large loss of filtered samples under vacuum filtration, it may be necessary to make the unfiltered sample several times and filter several times to collect a sufficient quantity of the target product. Loss of the sample affects the product yield, directly increasing research and development time, cost, manpower, and subsequent commercialization process design, timing and profitability. The design of short stem outlet can cause splashing and foaming of the filtered fluid in the receiving receptacle. Splashing and foaming can cause the filtered fluid sample change in the components or promote chemical reactions between substances. For example, splashing of the high temperature filtered fluid to the wall of the receiving receptacle can cause solid crystals precipitating from fluid or solution. Splashing and foaming can damage the components of the filtered samples, such as the structure of macromolecules, i.e. cells or proteins. Buchner funnels have been widely used; however, there is a lack of disposable filtration funnel with reasonably long outlet stem, a further lack of disposable filtration funnel with side-arm for vacuum connection and reasonably long outlet stem.

In some filtration operation, the filter paper and filter media are directly placed by a hand into a vacuum filtration funnel, the solid particles in the solid-liquid sample can flow or leak from the gap between the outer edge of the filter media and the inner bottom plate or the inner sidewall of the filtration funnel to the receiving receptacle, causing the particle leakages and the resultant failure of the effective filtration and separation. In addition, an increase in the thickness of filter cake dramatically accelerates the blockage and obstruction. The smaller the pore size of the filter membranes and frits, the more pores are clogged. When the pores are partially and severely clogged, the filter membrane or filter frits and the receiving receptacle are exposed to strong vacuum conditions. Under strong vacuum conditions, the filter paper and thin filter membrane, even sealed to the bottom of the filtration funnel, can break or crack at the seal, causing the particles and unfiltered sample sucked into the receiving receptacle and severely impacting the filtration and separation. U.S. Pat. No. 4,702,834 discloses a filter membrane welded to the inner bottom of the filtration funnel with a weld width of 2.29 mm. U.S. Pat. No. 7,011,755 discloses a funnel with a final filter and integral prefilter which have one or more layers of prefilter material. The final filter at the bottom is sealed to the funnel; however, all the prefilters contact the funnel with non-absolute or releasable seal rings, allowing the passage of unfiltered sample. In forgoing patents, the filter frits or membranes are sealed only to the inner bottom of the funnel, forming a single seal. The seal width is narrow and there is no protective seal. Practically, the sealing joints in the strong vacuum condition may crack, resulting in the unfiltered sample sucked to the receiving vessel. In some filtration operation, a proper mixing of the sample mixture in the funnel is necessary to improve filtration effectiveness and reduce the filtration time. The long stirring rods made of glass and plastic sometimes directly contact and inevitably damage the seal welded joints, eventually leading to the unfiltered sample sucked into the receiving receptacle. In addition, above filter frits or membranes and the funnel sometimes are made of different materials showing different melting properties, which are very difficult to form the leak-free seal, and only sealed to the inner bottom of the funnel without a protective seal. A slight crack on the seal welded joints can cause the unfiltered samples sucked into the receiving receptacle. U.S. Patent Application 20100038303 and Chinese Patent Application 2010800640629 disclose a disposable polymer-structured filtering kit, but the lack of a welded integration between the filter frit and the filtration funnel will cause the leakage of unfiltered sample under vacuum conditions.

Many of Buchner funnels used in the laboratory are in fact made of glass individually by hand, suggesting a high labor cost, relative high pricing, and easily-broken feature of all the glassware. Some large Buchner funnels are made of ceramic, relatively bulky and heavy, and inconvenient to move during use. A few user-convenient filtration funnels have been developed, such as combined plastic Buchner funnels from SIGMA in the United States. However, all these funnels have no side-arms for connection to the vacuum source, need rubber gasket to seal, and not convenient to use. U.S. Patent Application 20100038303 and Chinese Patent Application 2010800640629 disclosures a filtration funnel which needs to connect with an external glass-made side-arm in application and not convenient.

In a summary, all these prior art techniques have the forgoing drawbacks. In the practical filtration, the solid materials as filter cake are target product to be collected, and sometimes the filtered fluid as filtrate to be collected, and sometimes both solid materials and filtered fluid to be collected. Therefore, there is a practical need for the object of the present invention to provide a cost-effective disposable vacuum filtration funnel to reduce or eliminate the loss of filtrate and filter cake, avoid contamination, and reduce filtration costs and time.

SUMMARY OF THE INVENTION

The invention is aimed at providing a disposable integrated polymeric vacuum filtration funnel to overcome the drawbacks of the existing disposable filtration funnels, such as loss of filtrate and filter cake, contamination to the filtered sample, inconvenient to use, and expensive.

The technical approach solving the forgoing drawbacks in this invention is:

A disposable integrated polymeric vacuum filtration funnel.
  The disposable integrated polymeric vacuum filtration funnel comprise a filtration funnel body having a filter frit disposed inside at the bottom, an outlet stem connected with an outlet at the outer bottom of the filtration funnel body, the outlet stem integrated with the filtration funnel body, the filter frit sealed to the inner bottom and the inner side surface of the filtration funnel body;
  A disposable integrated polymeric vacuum filtration funnel comprise a sealing joint disposed underneath the outer bottom of the filtration funnel body, the sealing joint having a side-arm for vacuum connection and a standard adaptor to connect the receiving receptacle,
  The outlet stem protruding from the standard adaptor,
  The filter frit, the filtration funnel body, and the sealing joint are integrated as one device.

Further, a seal press ring is disposed onto the filter frit; in addition to the seal connection between the filter frit and the filtration funnel body, it is preferred to use the seal press ring to have a double seal thus improving seal effectiveness.

Preferably, the filter frit is welded to the inner bottom and the inner surface of the filtration funnel body, the outlet stem and the sealing joint both are welded to the outer bottom of the filtration funnel body. Welding is the preferred means to form an integrated structure and other suitable integration or assembly means can also be used. This embodiment just uses the filter frit in the absence of the seal press ring.

In an alternative embodiment, the filter frit is welded to the inner bottom and the inner surface of the filtration funnel body, the seal press ring is welded to the filter frit and the adjacent inner surface of the filtration funnel body, both the outlet stem and the sealing joint are welded to the outer bottom of the filtration funnel body. As compared to previous embodiment not using the seal press ring, this embodiment uses the seal press ring followed by leak-free welding, providing a protective seal.

In a further preferred embodiment, the filtration funnel body includes an open inlet and a reservoir for holding unfiltered sample therein, the reservoir having support ribs, diversion channels and filtering frit groove inside at the bottom, the support ribs distributed inside at the bottom of the reservoir outwardly from the outer periphery of the outlet hole to the adjacent inner wall of the reservoir, the diversion channels in between adjacent support ribs, the filter frit embedded in the filter frit groove, the bottom surface of the filter frit bound on the top surface of the support ribs, the outer side surface of the filter frit in seal contact with the inner surface of the side wall at the bottom of the reservoir. The embodiment illustrates a preferred sealing assembly to integrate a cylindrical filtration funnel with filter frit having a leak-free seal. However, other proper integration means can be used to achieve the leak-free assembly.

In an alternative embodiment, the filtration funnel body includes an open inlet and a reservoir for holding unfiltered sample therein, the reservoir having the support ribs, the diversion channels, the filtering frit groove and step inside at the bottom, the support ribs distributed inside at the bottom of the reservoir outwardly from the outer periphery of the outlet hole to the adjacent inner wall of the reservoir, the diversion channels in between adjacent support ribs, the step recessed inwardly from inner wall of the reservoir at the bottom, the filter frit embedded in the filter frit groove, the bottom surface of the filter frit bound on the top surface of the support ribs, the outer side surface of the filter frit in seal contact with the inner side surface of the step, the bottom surface of the seal press ring bound on the top surfaces of the filter frit and the step, the outer side surface of the seal press ring in seal contact with the inner surface of the side wall at the bottom of the reservoir. The embodiment illustrates a preferred sealing assembly to integrate a cylindrical filtration funnel body with the filter frit and the seal press ring having a leak-free seal. Other proper integration means can be used to achieve the leak-free assembly.

As another preferred embodiment, the integration means between the filtration funnel body and the sealing joint, includes but not limited to one of concave-convex assembly, concave-convex welding assembly, ultrasonic welding, spin welding, heat welding, radio frequency sealing, adhesive bonding, solvent seals, thread seal, seal ring seal, thread engagement, thread engagement with gasket, tongue-and-groove assembly, and the wedged assembly, or any combination of two or more thereof.

Preferably, the outer bottom of the filtration funnel body has a downward connecting member, the sealing joint has a inner lumen on the top, the connecting member of the filtration funnel body inserts into the inner lumen of the sealing joint forming to achieve a leak-free connection. The connecting member comprises a convex-like or groove-like connecting section. The embodiment illiterates a seal assembly connecting a cylindrical filtration funnel body with the sealing joint to achieve a leak-free seal. Other types of suitable connecting members can be used to achieve the leak-free assembly.

Further, the inner surface of the top lumen of the sealing joint is in seal contact with the outer surface of the connecting member protruding from the bottom of the filtration funnel body, the top surface of the top lumen of the sealing joint is in seal contact with the outer bottom surface of the filtration funnel body. Alternatively, the outer surface of the sealing joint is in seal contact with the inner surface of the groove of the connecting member protruding from the bottom of the filtration funnel body. The preferred embodiment illustrates a protrusion and sealing joints (i.e., convex-concave assembly methods), and the groove and sealing joints (i.e., concave on the convex assembly methods). Other types of engagement mechanism can be used to achieve the leak-free assembly.

Preferably, the filtration funnel body, the funnel outlet stem, and the sealing joint are made of polymer materials, including polyethylene, polypropylene, polystyrene, plastic, and rubber. The filter frit is made of porous filter media or porous membranes, including a variety of commonly used porous material or porous filter media. The filter frit material has a pore size less than 1 mm, preferably less than 500 microns, more preferred less than 25 microns.

More preferably, the filtration funnel body, the funnel outlet stem, the sealing joint, and the seal press ring are made of polymer materials, including polyethylene, polypropylene, polystyrene, plastic, and rubber. The filter frit is made of porous filter media or porous membranes. The filter frit material has a pore size less than 1 mm, preferably less than 500 microns, more preferred less than 25 microns.

In a further preferred embodiment, the top surface of the filter frit steps up the top surface of the step a height from 0.1 mm to 5 mm, preferably 0.3 mm, which can increase the seal between the filter frit, the step, the seal press ring, and the corresponding contact surfaces.

In a still further preferred embodiment, the seal press ring has protrusion on the bottom. The protrusion presses against the top surface of the filter frit, increasing the seal between the filter frit, the seal press ring, and the corresponding contact surfaces. One or more than one set of protrusion can be used to reach better seal. In the present invention, one set of protrusion can meet the seal requirements.

In a another preferred embodiment, the outlet stem of the filtration funnel enters into the receiving receptacle, the outlet tip of the outlet stem can be toward near the inner bottom of the receiving receptacle, and the side-arm is reasonably far away from the outlet tip. In this embodiment, the outlet tip of the outlet stem positions at much lower than side-arm, considerably reducing or completely eliminating the fluid loss to the vacuum suction. Meanwhile, the outlet tip of the long outlet stem toward near the bottom of the receiving receptacle can reduce or avoid fluid sample splashing and resultant sample damage.

Preferably, the outlet stein of the filtration funnel can connect to an extension tube in order to be close to the inner bottom of the receiving receptacle. In this embodiment, the length of the outlet stem can be cut to reduce length or connected with one or more extension tubes to extend length depending on the fluid property and depth of the receiving receptacle. Practically, the outlet stem can be cut short to accommodate the shallow depth or height of the receiving receptacle. The use of plastic material to make outlet stem allows the ease of cutting. In an embodiment (not shown) of the present invention, the long outlet stem can be pre-cut annularly from the tube outside toward inside for convenient application. The pre-cut depth is about a third of the wall thickness of the outlet steam but not more than two thirds, for the end-user to easily break and save time.

Further preferably, the standard adaptor is an externally ground joint. In this embodiment, the standard adaptor is a standard ground joint, especially a standard externally ground joint to conveniently fit into a standard internally ground joint of the receiving receptacle and easily disconnect. Standard ground flasks, Erlenmeyer flasks, and storage bottles are the most common and popular receiving receptacles among the laboratory vessels, far more widely used than threaded receiving flasks. In this embodiment, the sealing joint uses a standard ground joint, especially a standard taper-ground inner joint to directly fit into a standard taper-ground outer joint of the flask, Erlenmeyer flask, or storage bottle. This does not require a specially designed receiving receptacle, significantly increases the applicability and convenience, and eliminates the purchase requirement of specially-designed receiving receptacle and related cost. Other connection types can be also used for the sealing joint, including a threaded connection. However, the threaded connection could not directly fit into the commonly used laboratory receiving receptacle, such as round and flat bottom flask, Erlenmeyer flask, and storage bottle, significantly reducing the applicability and popularity.

A further alternative preferred embodiment, the filtration funnel body has an inverted conical shape; the filtration funnel body comprises step, short support ribs, long support ribs, diversion channels, and the fluid collection groove; the step is arranged at the bottom of the filtration funnel body; the short and long support ribs are arranged inwardly from the step; the short support ribs and long support ribs are arranged in a pattern to create the diversion channels which are void space between the support ribs; the diversion channels are in fluid flow communication with the fluid collection groove; the fluid collection groove is in fluid flow communication with the interior of the bottom outlet hole;

the bottom surface of the filter frit binds on the top surfaces of the short and long support ribs; the outer side surface of the filter frit is in seal contact with the inward side surface of the step. The embodiment illustrates a preferred sealing assembly to integrate an inverted conical filtration funnel with filter frit having a leak-free seal. However, other proper integration means can be used to achieve the leak-free assembly.

Alternatively, the filtration funnel body has an inverted conical shape; the filtration funnel body comprises top step, bottom step, short support ribs, long support ribs, diversion channels, and the fluid collection groove; the first and bottom steps are sequentially arranged at the bottom of the filtration funnel body; the short and long support ribs are arranged inwardly from the bottom step; the short support ribs and long support ribs are arranged in a pattern to create the diversion channels which are void space between the support ribs; the diversion channels are in fluid flow communication with the fluid collection groove; the fluid collection groove is in fluid flow communication with the interior of the bottom outlet tube; the bottom surface of the filter frit binds on the top surfaces of the short and long support ribs; the outer side surface of the filter frit is in seal contact with the inward side surface of the bottom step; the bottom surface of the seal press ring binds on the top surfaces of the filter frit and the bottom step; the outer side surface of the seal press ring is in seal contact with the inward side surface of the top step. The embodiment illustrates a preferred sealing assembly to integrate an inverted conical filtration funnel body with the filter frit and the seal press ring having a leak-free seal. However, other proper integration means can be used to achieve the leak-free assembly.

Further, the cross section of the filtration funnel body can be round, oval, trapezoidal, square, rectangular, and conical, or any combination of two or more thereof. The filtration funnel body could also be other irregular shapes.

Furthermore, the cross section of the filtration funnel body can be round, complete or partial quadrilateral, oval, trapezoidal, diamond, square, and rectangular, or combination of two or more thereof. The cross section of the filtration funnel body could also be other irregular shapes.

Still furthermore, the seal press ring can be round, complete or partial quadrilateral annular, oval ring, trapezoidal ring, diamond ring, square ring, and rectangular ring, or combination of two or more thereof. The seal press ring could also be other irregular shapes.

Still furthermore, the cross section of the seal press ring can be triangular, complete or partial circular, oval, trapezoidal, square, rectangular, or combination of two or more thereof. The cross section of the seal press ring could also be other irregular shapes.

The protrusion of the seal press ring can be round annular, complete or partial quadrilateral annular, oval ring, trapezoidal ring, diamond ring, square ring, and rectangular ring, or combination of two or more thereof; the protrusion of the seal press ring can be the same or similar shape to the seal press ring. The protrusion of the seal press ring could also be other irregular shapes.

Preferably, the welding is ultrasonic welding, but can be heat welding, spin welding, radio frequency sealing, or combination of two or more thereof; the welding could also be other suitable welding techniques.

The beneficial effects of the present invention are to effectively reduce or eliminate the loss of filtrate and filter cake, avoid contamination, easy to use and cost-effective.

BRIEF DESCRIPTION OF THE DRAWINGS

FIG. 3A is a top view of the filtration funnel body 100 depicted in FIG. 1A.

FIG. 3B is a perspective view (top and side view) of the filtration funnel body 100 depicted in FIG. 1A.

FIG. 3C is a perspective view (bottom and side view) of the filtration funnel body 100 depicted in FIG. 1A.

FIG. 6A is a top view of an alternative seal press ring 320.

FIG. 6B is an isometric view having portions thereof removed, of an alternative seal press ring 320 depicted in FIG. 6A.

FIG. 6C is an enlarged partial cross-sectional view of the circled area depicted in FIG. 6B.

FIG. 8A is a top view of the sealing joint 400 with side-arm to connect vacuum and externally ground joint depicted in FIG. 1A.

FIG. 8B is a cross-sectional view of the sealing joint 400 with side-arm to connect vacuum and externally ground joint depicted in FIGS. 8A and 1A.

FIG. 8C is a perspective view (bottom and side view) of the sealing joint 400 with side-arm to connect vacuum and externally ground joint depicted in FIGS. 8A and 1A.

FIG. 9A is a cross-sectional view of the assembly of the filtration funnel body 100 and the sealing joint 400 depicted in FIG. 1A.

FIG. 9B is an enlarged partial cross-sectional view of the circled area depicted in FIG. 9A.

FIG. 10A is a connection diagram of the disposable integrated polymeric vacuum filtration funnel 800 based on this invention fitting into a standard internally ground joint of the receiving flask, wherein the filtration funnel body having cylindrical shape with a flare, the seal adaptor having a externally ground joint, and the outlet tip of the long outlet stem of the filtration funnel toward near the inner bottom of the receiving flask.

FIG. 10B is a perspective view of the extension tube 700 that can be connected to the outlet stem 106 of the disposable integrated polymeric vacuum filtration funnel 800 in this invention.

FIG. 10C is a connection diagram of the disposable integrated polymeric vacuum filtration funnel 800 based on this invention fitting into a standard internally ground joint of the receiving flask, wherein the filtration funnel body having cylindrical shape with a flare, the seal adaptor having a externally ground joint, and the outlet stem of the filtration funnel connecting to an extension tube in order to toward near the inner bottom of the receiving flask.

FIG. 11A is a top view of another conventional filtration funnel with an inverted cone shape.

FIG. 11B is a perspective view (top and side view) of the conventional filtration funnel with an inverted cone shape depicted in FIG. 11A.

FIG. 11C is a perspective view (bottom and side view) of the conventional filtration funnel with an inverted cone shape depicted in FIG. 11A.

FIG. 12A is a cross-sectional view of the filtration funnel 500 depicted in FIGS. 11A, 11B, and 11C, with a cutting plane line AA' as shown in FIG. 11A.

FIG. 12B is an enlarged partial cross-sectional view of the circled area depicted in FIG. 12A.

FIG. 13A is a perspective view of the disposable integrated polymeric vacuum filtration funnel with an inverted cone shape in this invention.

FIG. 13B is a cross-sectional view of the disposable integrated polymeric vacuum filtration funnel with an inverted cone shape depicted in FIG. 13A.

FIG. 14A is a connection diagram of the disposable integrated polymeric vacuum filtration funnel based on this invention fitting into a standard internally ground joint of the receiving flask, wherein the filtration funnel body having cylindrical shape with a flare, the seal adaptor having a externally ground joint, and the long outlet stem of the filtration funnel cut from pre-cut line to avoid close to the inner bottom of the receiving flask.

FIG. 14B is a connection diagram of the disposable integrated polymeric vacuum filtration funnel based on this invention fitting into a standard internally ground joint of the receiving Erlenmeyer flask, wherein the filtration funnel body having cylindrical shape without a flare, the seal adaptor having a externally ground joint, and the long outlet stem of the filtration funnel cut from pre-cut line to avoid close to the inner bottom of the receiving flask.

DETAILED DESCRIPTION OF THE PREFERRED EMBODIMENTS

Figures 1A, 1B:
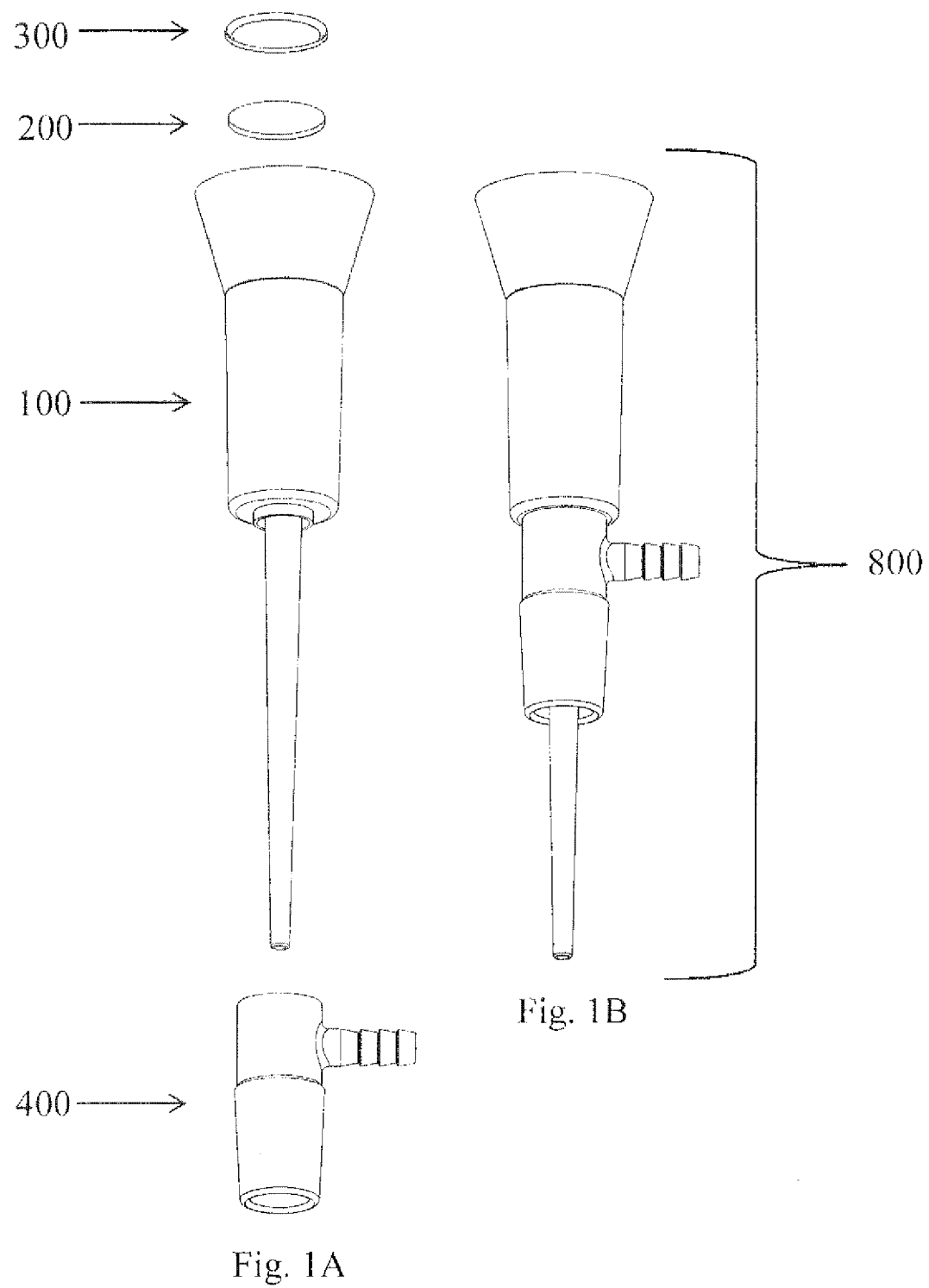
FIG. 1A is a perspective view of the four components used to assembly the disposable integrated polymeric vacuum filtration funnel based on this invention.
FIG. 1B is a perspective view of the disposable integrated polymeric vacuum filtration funnel welding-assembled using four components depicted in FIG. 1A.

The disposable integrated polymeric vacuum filtration funnels constructed in accordance with the principles of the present invention are illustrated in FIG. 1A through FIG. 15B.

Referring to FIG. 1A through FIG. 10C, a disposable integrated polymeric vacuum filtration funnel includes a filtration funnel body 100, a filter frit 200 disposed inside at the bottom of filtration funnel body 100, an outlet stem 106 extending out from the outer bottom of filtration funnel body 100; the outlet stem 106 integrated with the filtration funnel body 100; the filter frit 200 sealed to the inner bottom and the inner surface of the filtration funnel body 100; The disposable integrated polymeric vacuum filtration funnel includes a sealing joint 400 disposed underneath the filtration funnel, the sealing joint 400 having a side-arm for vacuum connection and a standard adaptor to connect receiving receptacle; the outlet stem 106 protruding through the standard adaptor; the filter frit 200, the filtration funnel body 100 and the sealing joint 400 are integrated as one device.

Further, a seal ring 300 is pressed onto the filter frit 200. The filter frit 200 and filtration funnel body 100 are assembled having a leak-free seal. It is preferred to use the seal press ring 300 to have a double seal thus improving seal effectiveness.

Preferably, the filter frit 200 is welded onto the inner bottom surface and the bottom inner surface of the filtration funnel body 100, the outlet stem 106 and the sealing joint 400 are welded onto the outer bottom of the filtration funnel body. Welding is the preferred means to form an integrated structure and other suitable integration or assembly means can also be used. This embodiment just uses the filter frit in the absence of the seal press ring.

Alternatively, the filter frit 200 is welded onto the inner bottom and the inner side surface of the filtration funnel body 100, the seal ring 300 is welded onto to the outer periphery of the top surface of the filter frit 200 and adjacent inner surface of the filtration funnel body, the outlet stem 106 and the sealing joint 400 are welded onto the outer bottom of the filtration funnel body. As compared to previous embodiment not using the seal press ring, this embodiment uses the seal press ring followed by leak-free welding, providing a protective seal.

The foregoing fluid receiving receptacles can be a variety of containers, mainly glass and plastic containers.

FIG. 1A and FIG. 1B show perspective views of the four components of the disposable integrated polymeric vacuum filtration funnel and an welding-assembled filtration funnel, respectively, in this invention. The typical components as shown in FIG. 1A include a filtration funnel body 100, a filter frit 200, a seal ring 300, and a sealing joint 400. FIG. 1B shows a typical disposable integrated polymeric vacuum filtration funnel 800 assembled using the four components shown in FIG. 1A in accordance with the principles of the present invention. The filter frit 200 and the seal ring 300 are sequentially disposed inside at the bottom of the filtration funnel body 100, and then the sealing joint 400 is connected to the outer bottom of the filtration funnel body 100. The foregoing four components require proper connections, including but not limited to welding, to integrate into a typical disposable integrated polymeric vacuum filtration funnel 800. The special features of the vacuum filtration funnel include but not limited to integrated welding assembly and long outlet stem. The present invention as shown in FIG. 1A and FIG. 1B is further described by FIG. 1A through FIG. 10B.

Figures 2A, 2B:
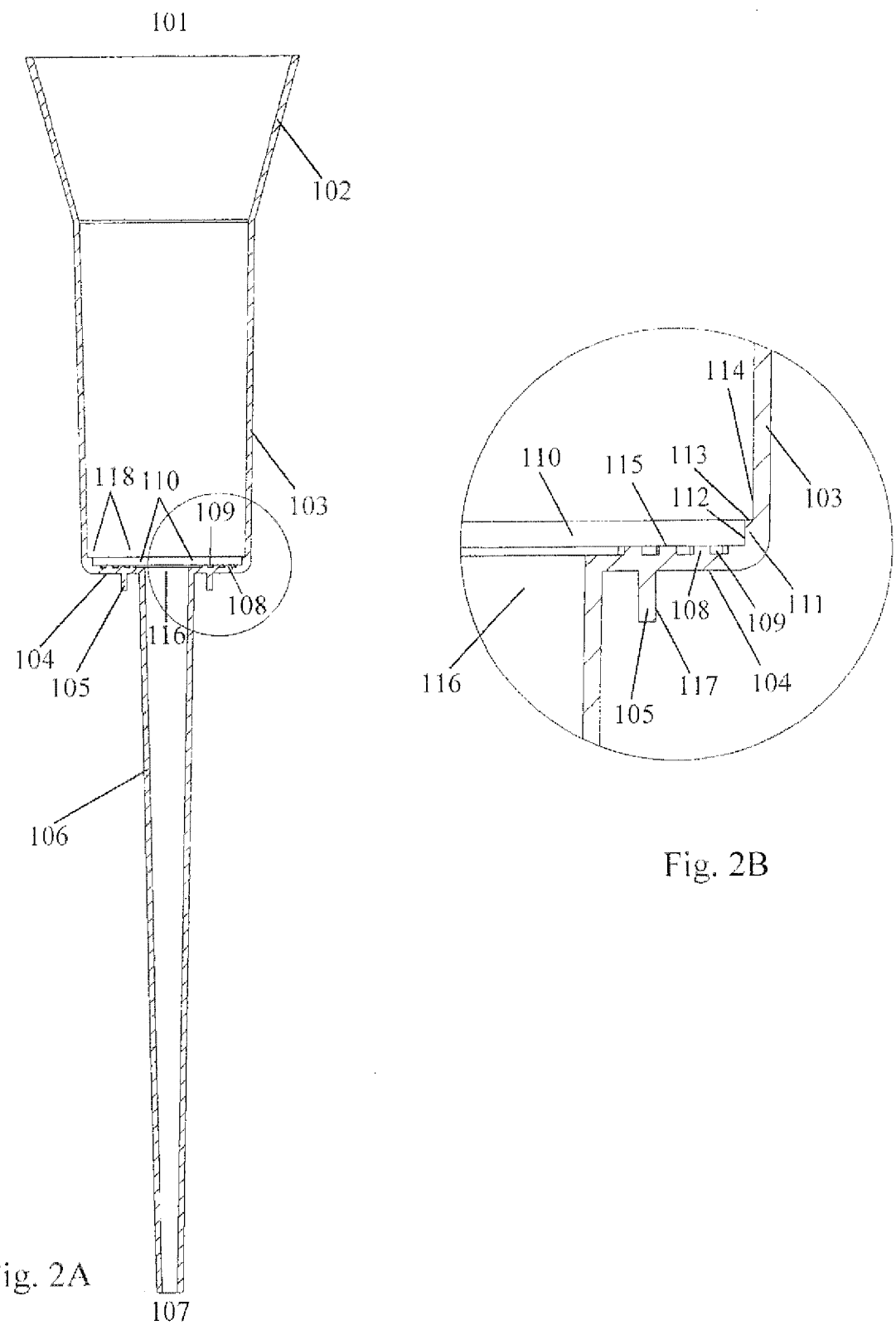
FIG. 2A is a cross-sectional view of the filtration funnel body 100 depicted in FIG. 1A.
FIG. 2B is an enlarged partial cross-sectional view of the circled area depicted in FIG. 2A.

FIG. 2A is a cross-sectional view of the filtration funnel body 100 depicted in FIG. 1A in this invention. The filtration funnel body 100 has an open inlet 101, a flare 102, a cylinder 103, an outer bottom surface 104, protrusion 105 protruding from the outer bottom surface 104, support ribs 108, diversion channels 109, filter frit grooves 110, a long outlet stem 106, and outlet tip 107. FIG. 2B is an enlarged cross-sectional view of the circled portion depicted in FIG. 2A. Referring to FIG. 2B, the filtration funnel at the inner bottom contains support ribs 108, diversion channels 109, a filter frit groove 110, a step 111, a side surface 112 of step 111, a top surface 113 of step 111, an inner surface 114 near the bottom of cylinder 103, a top surface 115 of support ribs 108, an outlet hole 116 centered at the bottom of the filtration funnel body, and an outer side surface 117 of protrusion 105. As further shown in FIG. 2B, the horizontal plane of top surface 113 of step 111 extends toward the center of the funnel and meets with inner surface 114 of cylinder 103, forming a seal press ring groove 118. The seal press ring groove 118 has a diameter equal to the filtration funnel bottom diameter. The filtration funnel has a long outlet stem 106 as shown in the FIG. 1A through FIG. 2B. The volume of the filtration funnel comprises a cylinder 103 and a flare 102; the unfiltered sample is as much as possibly or mainly stored inside the cylinder 103. The volume of the filtration funnel 100 is determined based on the quantity of mixture sample and filtration times needed to complete the filtration.

FIG. 3A, FIG. 3B, and FIG. 3C show the top view and perspective views of the filtration funnel body 100 depicted in FIG. 1A, respectively. It can be further seen there are support ribs 108 at different lengths, diversion channels 109, a flare 102, a top surface 113 of step 111, a cylinder 103, a bottom outer surface 104 of cylinder 103, annular protrusion 105 underneath the bottom of the cylinder, and a long outlet stem 106. The support ribs 108 at the bottom are designed to facilitate supporting the filter frit 200 and mixture samples; diversion channels 109 are designed to facilitate fluid passing through the filter frit 200, converging to funnel center outlet hole 116, passing long outlet stem 106, and exiting the outlet tip 107. The filtration funnel body 100 has a cylindrical shape and can also be a plurality of cylindrical or other shapes having the same functionality. The filtration funnel body 100 can also be a combination of two or more components having the same functionality, such as a combination of cylinder 103 and a long outlet stem 106, including any combination of threaded or welded assembly thereof. The filtration funnel body 100 is preferably made from polymer materials, including but not limited to polyethylene, polypropylene, polystyrene, etc., and can also be made from other suitable materials having the same functionality, including but not limited to plastics and rubber etc. It is preferably made from one of polyethylene, polypropylene, polystyrene and other polymer materials, or any combination thereof, to achieve disposable and cost-effective performance.

Figure 4C:
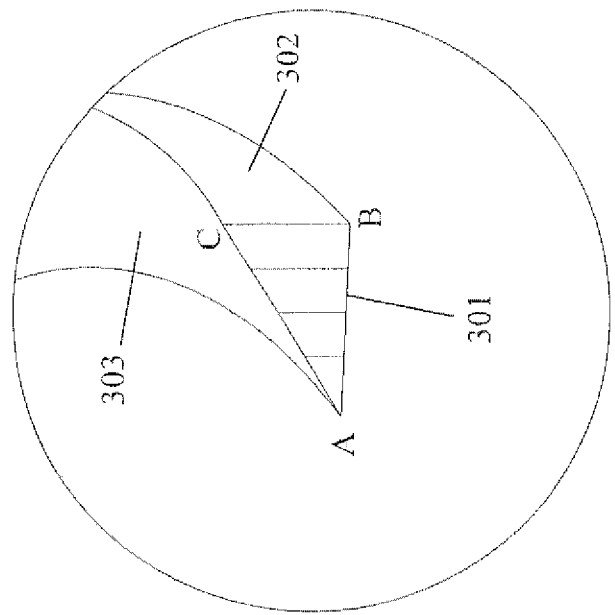
FIG. 4C is an enlarged partial cross-sectional view of the circled area depicted in FIG. 4B.
Figure 4A:
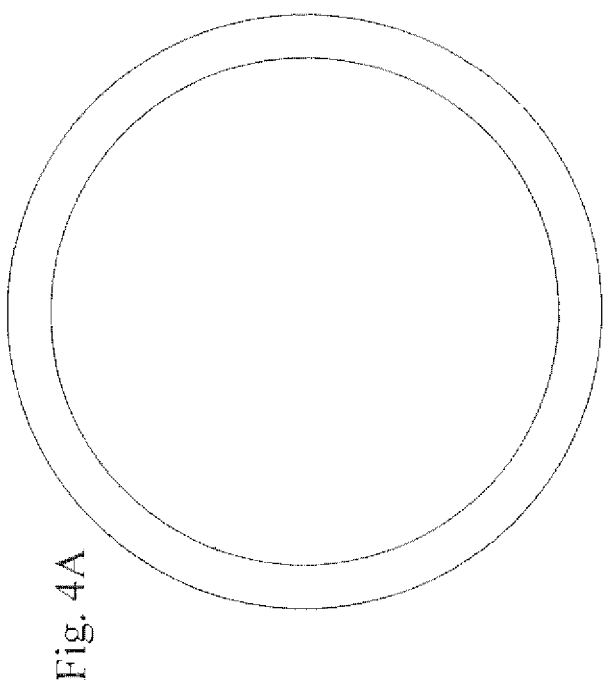
FIG. 4A is a top view of the seal press ring 300 depicted in FIG. 1A.
Figure 4B:
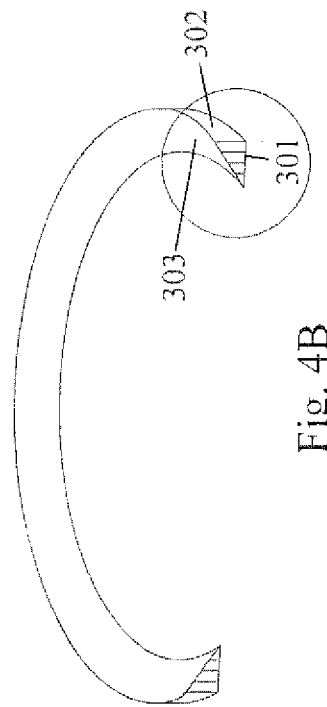
FIG. 4B is an isometric view having portions thereof removed, of the seal press ring 300 depicted in FIG. 1A.

FIG. 4A, FIG. 4B, and FIG. 4C show the top view, isometric view, and an enlarged partial cross-sectional view of the seal press ring 300 depicted in FIG. 1A, respectively. The seal press ring 300 includes a horizontal bottom surface 301, an outer side surface 302, and an inner side surface 303. The seal press ring 300 is an annular ring shape and it can also be other suitable shapes having the same functionality, including but not limited to one of full and partial quadrilateral annular, oval ring, trapezoidal ring, diamond ring, square ring, and rectangular ring, or any combination of two or more thereof. The cross section of the seal press ring as shown in FIG. 4B and FIG. 4C is right-angle triangle and it can also be other suitable shapes having the same functionality, including but not limited to one of full and partial round, oval, trapezoidal, diamond, square, and rectangular, or any combination of two or more thereof. The right-angle triangle ABC has a bottom edge AB, the hypotenuse AC, and the other right-angle side BC. The seal press ring is preferably made from polymer materials, including but not limited to polyethylene, polypropylene, polystyrene, etc., and can also be made from other suitable materials having the same functionality, including but not limited to plastics, rubber, and metal etc. Whenever possible, the seal press ring 300 should be made from materials similar to the filtration funnel body 100, and preferably from exactly the same materials as the filtration funnel body 100 in order to easily achieve the best performance of heat welding.

Figure 5B:
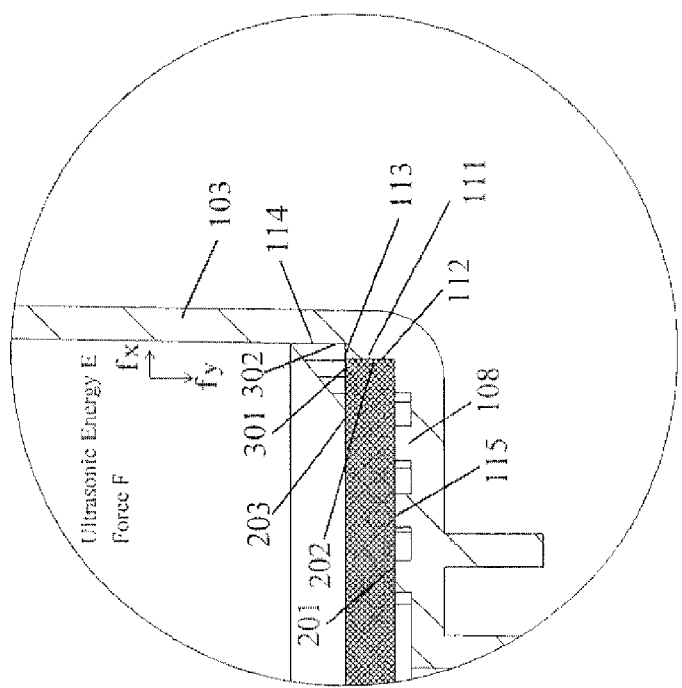
FIG. 5B is an enlarged cross-sectional view of the circled area depicted in FIG. 5A.
Figure 5A:
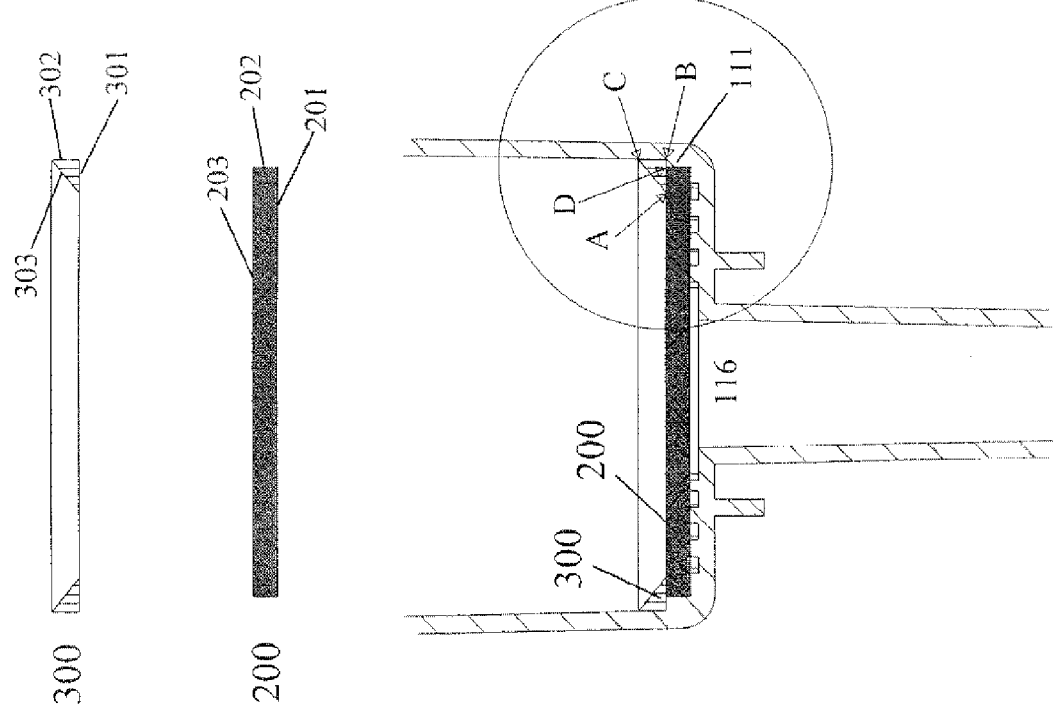
FIG. 5A is a cross-sectional view having portions thereof removed, of the assembly of the seal press ring 300, filter fit 200, and filtration funnel body 100 depicted in FIG. 1A, at the bottom of the filtration funnel body.

FIG. 5A and FIG. 5B show cross-sectional views of the filter frit 200, the seal press ring 300, and their assembly with the filtration funnel body 100 at the bottom of filtration funnel body and an enlarged cross-sectional view of the circled area depicted in FIG. 5A, respectively. Referring to FIG. 5A, the filter frit 200 is disposed into the filter frit groove 110; the shape and size of the filter frit are designed to exactly or substantially match the filter frit groove 110. Subsequently the seal press ring 300 is disposed onto the filter frit 200 and the step 111, into the seal press ring groove 118. Further referring to FIG. 5B, after the filter frit 200 is disposed into the filter frit groove 110, the horizontal bottom surface 201 of filter frit 200 contacts the top surface 115 of support ribs 108, and the outer side surface 202 of filter frit 200 contacts the inner side surface 112 of step 111. The shape and size of the filter frit 200 are designed to allow the outer side surface 202 of filter frit 200 in seal contact with the inner side surface 112 of step 111. Subsequently the seal press ring 300 is disposed onto the filter frit 200 and the step 111, the horizontal bottom surface 301 of seal press ring 300 contacts the top surface 203 of filter frit 200 and the top surface 113 of step 111, and the outer side surface 302 of seal press ring 300 contacts the inner surface 114 of cylinder 103 at the bottom. Referring to FIG. 5A shows a width AB of the bottom edge of annular seal press ring 300, a width DB of the bottom edge of annular step 111, and AB=AD+DB. AD is about three times of DB to as much as possibly avoid the filter frit 200 slipping out under external forces, but the ratio between AD and DB varying with the funnel volume can be rationally designed. To increase the effective filtration area and the filtration speed, the seal press ring 300 and the step 111 should be as small as possible, namely both AB and DB should be as small as possible under the preconditions of satisfying the following welding requirements. In order to further increase the sealing effectiveness among filter frit 200, steps 111, seal press ring 300, and the corresponding contact surfaces, the thickness of the filter frit 200 is designed to allow the top surface of filter frit 0.5 to 5 mm taller than the top surface of step 111, preferably 0.3 mm. Referring to FIG. 5A and FIG. 5B, the filtration funnel body 100, the filter frit 200, and the seal press ring 300 are assembled using specially designed craft equipment (not shown) followed by ultrasonic welding. In the presence of external force F, the ultrasonic energy E along with pressurized fx direction welds the outer side surface 302 of seal press ring 300 and the inner surface 114 together (CB welded surface), and along with pressurized fy direction welds a partial of bottom surface 301 of seal press ring 300 with the top surface 113 together (DB welded surface). Thereby, the ultrasonic welding gets the periphery and nearby edge of the top and bottom surfaces of filter frit 200 forced into an interspace among seal press ring 300, support ribs 108, and step 111, forming an integrated seal. Similarly, the ultrasonic welding can also get the seal press ring 300 and the top surface near the outer periphery of filter frit 200 welded together (AD welded surface) to form a leak-free connection, further welded together with filtration funnel body 100 to form an integrated seal. The ultrasonic welding is preferred to form leak-free connection among seal press ring 300, surface 113, surface 114, and filter frit 200 in this invention, but other leak-free connection means may be used including, but are not limited to, heat welding, spin welding, radio frequency sealing, adhesive bonding, solvent sealing, and gasket sealing et al., or any combination of two or more thereof. The forgoing ultrasonic welding integrates the filter frit 200 and funnel cylinder 103 as one device having two additional welded surfaces DB and CB and strengthens the seal between them, eliminating the breaks of contact surfaces between filter frit and funnel cylinder and resultant unfiltered sample leakage. The suction power in vacuum filtration practice is main driving force to pull sample through the filter media, but the suction power intensity and duration typically are not sufficient to break above two welded surfaces. In addition to the welded surface AD, the design in this invention shows a welded surface DB at the bottom inside the filtration funnel and a welded surface CB at the bottom near the inner wall of the filtration funnel, forming double seals. As long as only one of two welded surfaces DB and CB does not completely break, the filter frit 200 remains pressed underneath the seal press ring 300 and sealed with the step 111, suppressing unfiltered sample leakage.

When the sample to be filtered, such as liquid and solid mixture, is poured into the filtration funnel body 100, liquid or fluid passes successively through filter frit 200 and diversion channels 109, converges to center outlet hole 116, flows along with the long outlet stem 106, exits outlet tip 107 into receiving receptacle; while the unpassed materials such as solids remains left on the top surface of filter frit 200; thereby the separation of the solid and liquid or fluid is achieved.

The filter frit 200 is preferred made from porous filter media materials, including a variety of porous polymer materials that can prevent solid particles contained in the fluid from filtering through and support the filter cake and solid particles, further including, but not limited to, polyethylene, polypropylene, polystyrene et al., and porous separation membrane materials, still further including, but not limited to mixed cellulose membrane, nylon, polytetrafluoroethylene membrane, polyvinylidene fluoride, polyether, and it can also be other suitable materials having the same functionality, including, but not limited to plastics and rubber. The pore size of filter frit material is less than 1 mm, preferred less than 500 microns, more preferred less than 25 microns.

The seal press ringing 300 shown in FIG. 4A, FIG. 4B, and FIG. 4C is an example for illustrative purposes only. A person skilled in the art will know, without departing from the scope of the present invention, other variations and modifications are possible. For example, FIG. 6A, FIG. 6B, and FIG. 6C show a top view, an isometric view, and an enlarged cross-sectional view of an alternative seal press ring 320, respectively. The seal press ring 320 includes a horizontal bottom surface 321, protrusion 324 of horizontal bottom surface 321, an outer side surface 322, and an inner side surface 323. The seal press ring 320 is an annular ring shape and it can also be other suitable shapes having the same functionality, including but not limited to one of full and partial quadrilateral annular, oval ring, trapezoidal ring, square ring, and rectangular ring, or any combination of two or more thereof. The protrusion 324 is an annular ring shape and it can also be other suitable shapes having the same functionality, including but not limited to one of full and partial quadrilateral annular, oval ring, trapezoidal ring, diamond ring, square ring, and rectangular ring, or any combination of two or more thereof; however, it should have a shape as similar as possible to the seal press ring 320, facilitating seal assembly. The cross section of the seal press ring as shown in FIG. 6B and FIG. 6C is right-angle triangle shape and it can also be other suitable shapes having the same functionality, including but not limited to one of full and partial round, oval, trapezoidal, diamond, square, and rectangular, or any combination of two or more thereof. The right-angle triangle LMN as shown has a bottom edge LM, the hypotenuse LN, and the other right-angle side MN. Relative to the bottom edge LM, the height of protrusion 324 is less than that of right-angle side MN, preferably less than half the height of right-angle side MN but not less than 0.3 mm. The protrusion 324 can be one or more to achieve better sealing effectiveness. One protrusion 324 in this invention can basically meet the sealing requirements. The seal press ring 320 is preferably made from polymer materials, including but not limited to polyethylene, polypropylene, polystyrene, etc., and can also be made from other suitable plastics having the same functionality, including but not limited to rubber and metal etc. Whenever possible, the seal press ring 320 should be made from materials similar to the filtration funnel body 100, and preferably from exactly the same materials as the filtration funnel body 100 in order to easily achieve the best performance of heat welding.

Figure 7:
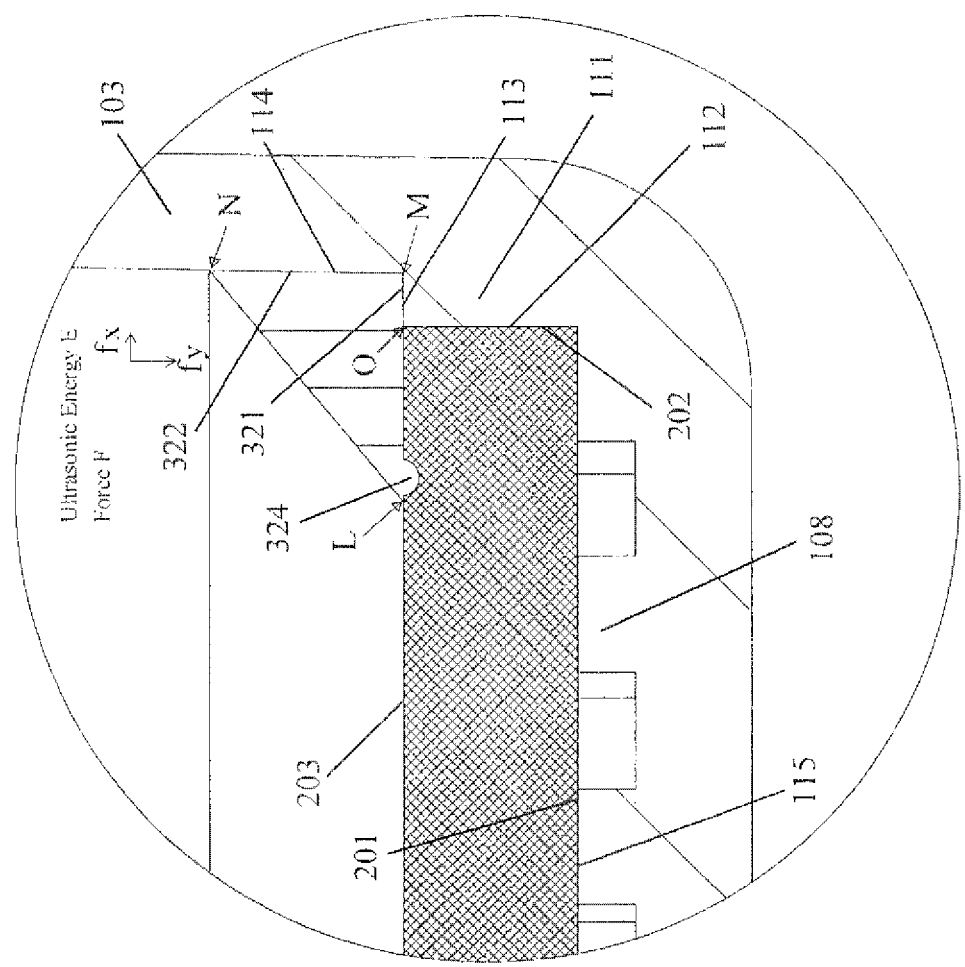
FIG. 7 is an enlarged partial cross-sectional view having portions thereof removed, of the assembly of the filter frit 200, an alternative seal press ring 320, and the filtration funnel body 100 at the bottom of the filtration funnel body.

FIG. 7 is an enlarged partial cross-sectional view of the assembly of the filter frit 200, an alternative seal press ring 320 shown in FIG. 6A through FIG. 6C, and the filtration funnel body 100 at the bottom of the filtration funnel body. Similarly as shown in FIG. 5A and FIG. 5B, referring to FIG. 7, the filtration funnel body 100, the filter frit 200, and the seal press ring 320 are assembled using specially designed craft equipment (not shown) followed by ultrasonic welding. In the presence of external force F, the ultrasonic energy E along with pressurized fx direction welds the outer side surface 322 of seal press ring 320 with the inner surface 114 together (MN welded surface), and along with pressurized fy direction welds a partial of bottom surface 321 of seal press ring 320 with the top surface 113 together (OM welded surface). As compared to shown in FIG. 5B, the protrusion 324 of seal press ring 320 as shown in FIG. 7 is pressed down, by pressurized ultrasonic welding, into the filter frit 200, forming an additional seal, which first blocks the diffusion of fine particles from filtration funnel, through the bottom surface 321 of seal press ring, toward the interface between filter frit 200 and step 111, and meanwhile suppresses the migration of the fine particles between top surface 203 of filter frit and bottom surface 321 of seal press ring, further preventing possible leakage of fluids and fine particles. Thereby, the ultrasonic welding gets the periphery and nearby edge of the top and bottom surfaces of filter frit 200 forced into an interspace among seal press ring 320, support ribs 108, and step 111, forming an integrated seal. Furthermore, the protrusion 324 is pressed down into the filter frit 200, further locking in the filter frit 200 and preventing the filter frit 200 from moving and bending, even in the presence of very strong vacuum suction. Relative to the bottom edge LM, the height of protrusion 324 is less than that of right-angle side MN, preferably less than half the height of right-angle side MN but not less than 0.3 mm, and also less than half the thickness of the filter frit 200. Similarly, the ultrasonic welding can also get the seal press ring 320 and the top surface near the outer periphery of filter frit 200 welded together (LO welded surface) to form a leak-free connection, further welded together with filtration funnel body 100 to form an integrated seal. The ultrasonic welding is preferred to form leak-free connection among seal press ring 320, surface 113, surface 114, and filter frit 200 in this invention, but other leak-free connection means may be used including, but are not limited to, heat welding, spin welding, radio frequency sealing, adhesive bonding, solvent sealing, and gasket sealing etc., or any combination of two or more thereof. The forgoing ultrasonic welding integrates the filter frit 200 and funnel cylinder 103 as one device having two additional welded surfaces OM and MN, constrains the filter frit from moving, and strengthens the seals and integration between them, eliminating unfiltered sample leakage caused from filter frit shifting and filter frit and cylinder contact surfaces breaking. The suction power in vacuum filtration practice is main driving force to pull sample through the filter media, but the suction power intensity and duration typically are not sufficient to break above two welded surfaces. In addition to the welded surface LO, the design in this invention shows a welded surface OM at the bottom inside the funnel and a welded surface MN at the bottom near the inner wall of filtration funnel, forming double seals; and protrusion 324 further prevents the filter frit from shifting and resultant two welded surfaces breaking. As long as only one of two welded surfaces OM and MN does not completely break, the filter frit 200 remains pressed underneath the seal press ring and sealed with the step 111, suppressing unfiltered sample leakage.

FIG. 8A, FIG. 8B, and FIG. 8C, are a top view, a cross-sectional view, and a perspective view of the sealing joint 400 with side-arm to connect vacuum and externally ground joint depicted in 1A, respectively. The sealing joint 400 includes an inlet 401 with top inner lumen, a top surface 402 of inlet connecting portion, an outlet adaptor 403, an exit 404, a side-arm 405 to connect to the vacuum source, a vacuum entrance 406, and an inner surface 407 of inner lumen at inlet connecting portion. The outlet adaptor 403 is illustrated as a standard ground joint, especially a standard externally ground joint to conveniently fit into a standard internally ground joint of the receiving receptacle and easily disconnect. Referring to FIG. 8A, FIG. 8B, and FIG. 8C, the inlet, outlet adaptor, and side-arm are one device, but it can also be an assembly, having the same functionality, of two components or any combination more than two components thereof. Standard ground flask, Erlenmeyer flask, and storage bottle are the most common and popular receiving receptacle among the laboratory vessels, far more widely used than threaded receiving flask. In this design, the sealing joint uses a standard ground joint, especially a standard taper-ground inner joint to directly fit into a standard taper-ground outer joint of the flask, Erlenmeyer flask, and storage bottle. This does not require a specially designed receiving receptacle, significantly increasing the applicability and convenience and eliminating the purchase requirement of specially-designed receiving receptacle and related cost. Other connection types can be also used for the sealing joint, including a threaded connection. However, the threaded connection could not directly fit into the commonly used laboratory receiving receptacle, such as round and flat bottom flask, Erlenmeyer flask, and storage bottle, significantly reducing the applicability and popularity.

FIG. 9A and FIG. 9B are a cross-sectional view of the assembly of filtration funnel body 100 and sealing joint 400 and an enlarged partial cross-sectional view, respectively. The protrusion 105 underneath the filtration funnel body 100 fits into the top inner lumen of inlet 401 of sealing joint 400 and the outer side surface 117 of protrusion 105 is in seal contact with inner surface 407 of top inner lumen of inlet 401. Spin welding is preferably used to seal the surface 117 and the surface 407 firmly in this invention to increase the sealing effectiveness. The protrusion 105 underneath the filtration funnel body 100, diameter of inner lumen of inlet 401, and shape and size of inner surface 407 can be appropriately designed in order to facilitate the welding operation and to achieve leak-free welding. Referring to FIG. 9A and FIG. 9B, the outer horizontal surface 104 underneath the filtration funnel body 100 is in contact with the horizontal top surface of 402 of inlet connection section of sealing joint 400, which can be similarly spin welded to form an additional leak-free seal.

In another obvious convex-concave assembly, the top diameter of the sealing joint 400 can be reasonably reduced so as to allow a direct insertion of top section of sealing joint 400 into protrusion 105, forming a seal contact between top outer wall (not shown) of sealing joint 400 and inner wall (not shown) of protrusion 105. The filter frit and seal press ring are not disposed inside the filtration funnel body 100, as shown in FIGS. 9A and 9B, to clearly show the assembly of filtration funnel body 100 and sealing joint 400, but the filter frit groove 110 and seal press ring groove 118 are clearly shown. By using specially designed craft equipment (not shown) in this invention, the integrated assembly of filtration funnel body 100, filter frit 200, and seal press ring 300 or 320, as shown in FIG. 5A and FIG. 5B, or FIG. 7, is assembled with sealing joint 400, as shown in FIG. 9A and FIG. 9B, followed by spin welding to weld sealing joint 400 and filtration funnel body 100 together. Other leak-free connection means may be used including, but are not limited to, spin welding, ultrasonic welding, heat welding, adhesive bonding, radio frequency sealing, solvent sealing, and gasket sealing et al., or any combination of two or more thereof.

Regarding the connection means of filtration funnel body 100 and sealing joint 400, the convex-concave assembly using annular protrusion 105 underneath the filtration funnel body 100 and inner lumen of inlet 401 is an example for illustrative purposes only. A person skilled in the art will know, without departing from the scope of the present invention, changing and modifying the shape and size of protrusion 105 and inlet 401 or even using other connection means are possible. For example, the annular protrusion 105 can be any other suitable shapes having the same functionality, including but not limited to one of full and partial circular ring, oval ring, trapezoidal ring, diamond ring, square ring, rectangular ring, a tapered ring, or any combination of two or more thereof. Accordingly, the inner lumen of inlet 401 of sealing joint 400, top surface 402 of inlet connecting portion, and surface 407 of inlet connecting portion can be properly changed and adjusted to facilitate the leak-free connection with protrusion 105 underneath the filtration funnel body 100. Another example, the annular protrusion 105 can also be substituted with proper concave groove recessed from the funnel bottom surface 104, preferred not recessed to perforating the bottom of filtration funnel body and communicating with the filter frit groove, but could communicate with filter frit groove. Accordingly, the wall thickness of inlet 401 of sealing joint 400, top surface 402 of inlet connecting portion, and surface 407 of inlet connecting portion can be properly changed and adjusted to facilitate the leak-free connection with concave groove recessed from the funnel bottom surface underneath the filtration funnel body 100. Still another example, outer side surface 117 of annular protrusion 105 can also use full or partial outer thread form, and then a corresponding inner thread form should be used for inner surface 407 of inlet connecting portion of sealing joint 400. Similarly, outer side surface 117 of annular protrusion 105 can also use full or partial inner thread form, and then a corresponding outer thread form should be used for outer surface (not shown) of inlet connecting portion of sealing joint 400. The protrusion 105 can even be removed, then the top surface 402 of inlet connecting portion of sealing joint 400 can be sealed onto outer surface 104 underneath the filtration funnel body 100 by using one of various means including but not limited to one of adhesive bonding, ultrasonic welding, heat welding, radio frequency sealing, or any combination of two or more thereof. The connection means of filtration funnel body 100 and sealing joint 400 can include, but not limited to one of conventional and improved concave-convex assembly, concave-convex welding assembly, ultrasonic welding, spin welding, heat welding, radio frequency sealing, adhesive bonding, solvent seals, thread seal, seal ring seal, thread engagement, thread engagement with gasket, tongue-and-groove assembly, and the wedged assembly, or any combination of two or more thereof.

FIG. 10A illustrates the connection diagram of a disposable integrated polymeric vacuum filtration funnel 800 in this invention and a standard ground joint flask 601, wherein the filtration funnel body having a cylindrical shape with a flare, the sealing joint having a externally ground joint, the flask 601 having a standard internally ground joint, and the outlet tip 107 of long outlet stem 106 of the filtration funnel toward near the inner bottom of the receiving flask 601. Referring to FIG. 10A, the standard ground joint flask has a standard ground height of H10 and a bottle-body depth (from ground ending line to the bottom of the flask bottle) H12. H12 is greater than H11. Generally, H12 is also greater than H10. Counting from the ground ending line downward toward the flask bottle bottom, the inserted length of funnel outlet stem into the flask bottle is H11. Ground flasks coming with different specifications and sizes, particularly those having large volumes or specially made may have different bottle-body depths. Thereby it is not possible to ensure one length H11 meet all requirements of ground flasks with varying specifications, including the flask body depth. FIG. 10B is a perspective view of extension tube 700 that can be connected to the outlet stem 106 of the disposable integrated polymeric vacuum filtration funnel 800 in this invention. FIG. 10C is a connection diagram of the disposable integrated polymeric vacuum filtration funnel 800 in this invention and a flask 602, wherein the filtration funnel body having cylindrical shape with a flare, the sealing joint having a externally ground joint, the flask 602 having a standard internally ground joint, and the long outlet stem 106 connecting to an extension tube 700 in order to toward near the inner bottom of the receiving flask 602. Comparing FIG. 10A and FIG. 10C, flask 602 has a volume greater than flask 601 and the same ground height (H20=H10) as flask 601, but the bottle body depth H22 of flask 602 is greater than the body depth H12 of flask 601. Referring to FIG. 10C, the funnel long outlet stem 106 connected to an extension tube 700 allows the outlet tip of funnel outlet stem 106 shift from 107A to 107B, significantly toward near the inner bottom of flask 602. The outlet tips 107 and 107B of long outlet stem 106 touching or nearly sealing the inner bottom of the flask will prevent filtration fluid from flowing out, offsetting or reducing the vacuum filtration speed and purpose. Referring to FIG. 10A and FIG. 10C, there are adequate clearances between the inner bottom of flask 601 and outlet tip 107 and between the inner bottom of flask 602 and outlet tip 107B in order to clearly show the outlet tips 107 and 107B neither close to, infinitely close to the bottom of the flask nor even touching the bottom of the flask to form nearly a seal. Referring to FIG. 10A and FIG. 10C, the seal adaptors with an externally ground joint of filtration funnel 800, a product in this invention, fit into internally ground joints of receiving flasks 601 and 602, respectively, forming leak-free seals through matching connections of externally ground joints of seal adaptors with internally ground joints of receiving flasks. The zigzag-shaped side-arm 405 is for connecting the vacuum hose to the vacuum source, such as a vacuum pump. Under the vacuum conditions, the sample to be filtered passes inlet 101, funnel cylinder 103 of integrated polymeric vacuum filtration funnel, and filter frit and long outlet stem 106 into the receiving flask, to achieve filtration and separation. The length of funnel outlet stem 106 is first preferred from 40 mm to 500 mm, particularly preferred from 60 mm to 400 mm, more particularly preferred from 80 mm to 200 mm. The length of extension tube 700 is first preferred from 100 mm to 400 mm, particularly preferred from 120 mm to 250 mm. The outlet stem can connect one or more extension tube 700, depending on the bottle body depth of receiving receptacle, to accommodate the deeper body depth of receiving receptacle. The outlet tip of the long outlet stem in this invention positions at much lower than side-arm, considerably reducing or completely eliminating the resultant sample loss being sucked away by vacuum. Meanwhile, the outlet tip of long outlet stem toward near the bottom of the receiving receptacle can reduce or avoid fluid splashing and resultant sample damage.

The filtration funnel body 100 can be a variety of shapes to store unfiltered sample mixture. Another typical shape can be a conventional inverted cone as shown in FIGS. 11A, 11B, and 11C. Referring to FIGS. 11A, 11B, and 11C, the conventional inverted conical funnel 500 has a top surface 501 of top step (513 not shown), a top surface 502 of bottom step (514 not shown), short support ribs 503*a*, 503*b*, 503*c*, 503*d*, 503*e*, 503*f*, long support ribs 504*a*, 504*b*, 504*c*, 504*d*, 504*e*, 504*f*, diversion channels 505 formed in the gap between support ribs, a fluid collection groove 506, a long outlet stem 507 with an outlet tip 508, an inner surface 509 and an outer surface 510 of the funnel reservoir, outer annular protrusion 511 at the outer bottom, and an outer surface 512. Different from conventional inverted conical funnel, the funnel in this invention has support ribs and steps at the inside bottom and annular protrusion 511 at the outer bottom. The top surfaces of above six short support ribs and six long support ribs are in the same horizontal plane, to facilitate supporting horizontally the filter frit. Six short support ribs and six long support ribs are shown in FIG. 11A and FIG. 11B. However, as long as supporting and diversion effectiveness can be reasonably achieved, the support ribs can be more or less than six and have different lengths and shapes.

FIG. 12A shows a cross-sectional view of the conventional filtration funnel 500 depicted in FIGS. 11A, 11B, and 11C, with a cutting plane line AA' vertically downward as shown in FIG. 11A. The conventional inverted conical funnel 500 has an inner surface 509 and an outer surface 510 of the funnel reservoir, outer annular protrusion 511 at the outer bottom, step 513 and step 514 connectedly located inside the bottom, a filter frit groove 515, and a seal press ring groove 516. FIG. 12B shows an enlarged partial cross-sectional view of the circled area depicted in FIG. 12A. Referring to FIG. 12B, the step 513 located inside the bottom has a top surface 501 and an inner side surface 517, the step 514 has a top surface 502 and an inner side surface 518, and the annular protrusion 511 has an outer surface 512. The filter frit 240 and seal press ring 340 are not disposed inside the filtration funnel, as shown in FIG. 12B, to clearly show the assembly of filtration funnel 500, filter frit 240, and seal press ring 340, and corresponding sealing interfaces and integration, but the filter frit groove 515 and seal press ring groove 516 are clearly labelled. Similarly to FIG. 5A, FIG. 5B, and FIG. 7, the filter frit 240 and the seal press ring 340, as shown in FIG. 12A and FIG. 12B, are substantially disposed into the filter flit groove 515 and the seal press ring groove 516 located inside the bottom of filtration funnel 500. The horizontal bottom surface of filter frit 240 contacts the top surface of support ribs located inside the bottom of filtration funnel and meanwhile the outer side surface of filter frit 240 contacts the inner side surface 518 of step 514. The shape and size of the filter flit 240 are designed to allow the filter frit exactly fit the filter flit groove. Subsequently the seal press ring 340 is disposed onto the filter frit 240 and the step 514, the horizontal bottom surface of seal press ring 340 contacts the top surface of filter frit 240 and the top surface 502 of step 514, and the outer side surface of seal press ring 340 contacts the inner surface 517 of step 513. The volume of the filtration funnel is determined based on the quantity of mixture sample and filtration times needed to complete the filtration. To increase the effective filtration area and the filtration speed, the distance UV from the outer periphery of seal press ring groove 516 to the inner surface 509 should be as small as possible under the preconditions of satisfying the following welding requirements, the distance ST from the filter frit groove to the outer periphery of seal press ring groove should also be as small as possible under the preconditions of satisfying the following welding requirements. Filter frit groove 515 and seal press ring groove 516 are concentric, but the diameter of filter frit groove 515 should be smaller than that of seal press ring groove 516. Length UV and ST varying with filtration funnel volume can be properly designed, preferably larger than 1 mm but not more than 20 mm, more preferably larger than 2.5 mm and less than 18 mm. The shape and size of the seal press ring 340 are designed to enable the seal press ring 340 exactly cover the contact gap and material interfaces between filter frit 240 and inner side surface 518 of step 514.

In order to further increase the sealing effectiveness among filter frit 240, step 514, seal press ring 340, and the corresponding contact surfaces, the thickness of the filter frit 240 is designed to allow top surface of the filter frit 0.1 to 5 mm taller than top surface of step 514, preferably 0.3 mm. Referring to FIG. 12B, the filtration funnel 500, the filter frit 240, and the seal press ring 340 are assembled using specially designed craft equipment (not shown) followed by ultrasonic welding. In the presence of external force F, the ultrasonic energy E along with pressurized fx direction welds together the outer side surface of seal press ring 340 and inner surface 517 of step 513 (UT welded surface) and along with pressurized fy direction welds together a partial of bottom surface of seal press ring 340 and top surface 502 of step 514 (ST welded surface). Thereby, the ultrasonic welding gets the periphery and nearby edge of the top and bottom surfaces of filter frit 240 forced into an interspace among seal press ring 340, support ribs 503*a*-503*f,* 504*a*-504*f,* and step 514, forming an integrated seal. Similarly, the ultrasonic welding can also get the seal press ring 340 and the top surface near the outer periphery of filter frit 240 welded together (welded surface not shown) to form a leak-free connection, further welded together with filtration funnel 500 to form an integrated seal. The ultrasonic welding is preferred to form leak-free connection among seal press ring 340, surfaces 517 and 502, and filter frit 240 in this invention, but other leak-free connection means may be used including, but are not limited to, heat welding, spin welding, radio frequency sealing, adhesive bonding, solvent sealing, and gasket sealing et al., or any combination of two or more thereof. The forgoing ultrasonic welding integrates the filter frit 240 and filtration funnel 500 as one device having two additional welded surfaces UT and ST and strengthens the seal between them, eliminating unfiltered sample leakage caused from filter frit and cylinder contact surfaces breaking. The suction power in vacuum filtration practice is main driving force to pull sample through the filter media, but the suction power intensity and duration typically are not sufficient to break above two welded surfaces. The design in this invention shows a welded surface ST located inside bottom of the funnel and a welded surface UT at the bottom near the inner wall of the funnel, forming double seals. As long as only one of two welded surfaces ST and UT does not completely break, the filter frit 240 remains pressed underneath the seal press ring and sealed with the step 514, suppressing unfiltered sample leakage. The seal press ring 340 (not shown) can be as shown in FIGS. 4A-4C and FIGS. 6A-6C or other suitable forms.

With respect to inclined inner surface 509 of filtration funnel 500, the shape of step 513 as shown in FIG. 12B is convex, but a concave shape or other suitable designed shapes can also achieve the leak-free purpose by using welding or other sealing means. Further, by increasing the diameter of filter frit groove 515 or reducing the diameter of seal press ring groove 516, as shown in FIG. 12B, the grooves 515 and 516 can be combined into one groove, forming an inverted cone funnel with one groove at inner bottom, wherein the point S, T, U in a downward vertical plane. As a consequence, a seal press ring should be properly designed and welded onto surface 501 and surface 509 located at inside bottom. Then the inverted conical funnel with one rationally designed groove, in accordance with assembly and welding principle shown in FIG. 5A, FIG. 5B, and FIG. 7 can also form an integrated assembly of filter frit, seal press ring, and filtration funnel.

FIG. 13A and FIG. 13B show a perspective view and a cross-sectional view of the disposable integrated polymeric vacuum filtration funnel with an inverted cone shape, respectively, in this invention. The filter frit 240 and the seal press ring 340 are sequentially disposed into the filter frit groove and the seal press ring groove located inside the bottom of filtration funnel 500 and followed by ultrasonic welding to weld together seal press ring 340, top surface of step 514, and inner side surface 512 of step 513, enabling the periphery and nearby edge of the top and bottom surfaces of filter frit 240 forced into an interspace among seal press ring 340, support ribs, and step 514, forming an integrally sealed assembly. Referring to FIG. 13B, the annular protrusion 511 underneath filtration funnel 500 fits into the top inner lumen of inlet 401 of sealing joint 400 and the outer side surface 512 of protrusion 511 is in seal contact with inner surface 407 of top inner lumen of inlet 401. The protrusion 511, the diameter of inner lumen of inlet 401, and shape and size of inner surface 407 can be appropriately designed in order to facilitate the welding operation and to achieve leak-free welding. In another obvious convex-concave assembly, the top diameter of the sealing joint 400 can be reasonably reduced so as to allow a direct insertion of top section of sealing joint 400 into protrusion 511, forming a seal contact between top outer wall (not shown) of sealing joint 400 and inner wall (not shown) of protrusion 511. By using specially designed craft equipment (not shown) in this invention, the integrated assembly of filtration funnel 500, filter frit 240, and seal press ring 340, as shown in FIG. 12B, is assembled with sealing joint 400, as shown in FIG. 13B, followed by spin welding to form an integrally sealed assembly. Other leak-free connection means may be used, including but are not limited to one of spin welding, ultrasonic welding, heat welding, adhesive bonding, radio frequency sealing, solvent sealing, and gasket sealing et al., or any combination of two or more thereof.

Regarding the connection means of filtration funnel 500 and sealing joint 400, the convex-concave assembly using annular protrusion 511 underneath filtration funnel body 500 and inner lumen of inlet 401 is an example for illustrative purposes only. A person skilled in the art will know, without departing from the scope of the present invention, changing and modifying the shape and size of protrusion 511 and inlet 401 or using other connection means are possible. For example, the annular protrusion 511 can be any other suitable shapes having the same functionality, including but not limited to one of full and partial circular ring, oval ring, trapezoidal ring, diamond ring, square ring, rectangular ring, a tapered ring, or any combination of two or more thereof. Above protrusion 511 can even be removed, then the top surface 402 of inlet connecting portion of sealing joint 400 can be sealed onto outer surface 510 of filtration funnel 500 by using one of various means including but not limited to one of adhesive bonding, ultrasonic welding, heat welding, radio frequency sealing, or any combination of two or more thereof. Similarly to forgoing connection means for funnel cylinder 100 and sealing joint 400, the connection means of filtration funnel 500 and sealing joint 400 can include, but not limited to one of conventional and improved concave-convex assembly, concave-convex welding assembly, ultrasonic welding, spin welding, heat welding, radio frequency sealing, adhesive bonding, solvent seals, thread seal, seal ring seal, thread engagement, thread engagement with gasket, tongue-and-groove assembly, and the wedged assembly, or any combination of two or more thereof.

It should be noted that although one filter frit is used in each illustration in this invention, one or any combination of more than one filter frit made with the same or different materials can be appropriately used.

FIGS. 14A, 14B, 15A, and 15B show additional connection diagrams of the disposable integrated polymeric vacuum filtration funnel in this invention fitting into internally ground joint of the receiving flasks. Referring to FIG. 14A, the seal adaptor with an externally ground joint of filtration funnel in this invention fits into an internally ground joint of receiving flask 603, forming leak-free seal through matching connection of externally ground joint of seal adaptor with internally ground joint of receiving flask. The zigzag-shaped side-arm 405 is for connecting the vacuum hose to the vacuum source, such as a vacuum pump. Under the vacuum conditions, the fluid sample passes inlet 101, funnel cylinder 103, filter frit and long outlet stem 106 into the receiving flask 603. The vacuum filtration funnel 100 in this invention can have a cylinder 103 but not have a flare 102 on the top as shown in FIG. 14B. Referring to FIGS. 1A-1B, FIGS. 8A-8C, FIGS. 9A-9B, FIGS. 10A-10B, FIGS. 13A-13B, FIGS. 14A-14B, and FIGS. 15A-15B, all these sealing joints 400 are externally ground joints, preferably international standard ground joints, such as 14/20, 24/40, 29/42, etc., more preferably to shorten the length of ground joint under the preconditions of keeping the same top outer diameter and taper angle of ground joint, such as 24/20 and 14/10. An externally ground joint is a preferred form of sealing joint underneath the vacuum filtration funnel while an internally ground joint is a preferred form of entrance joint of the receiving receptacle. Other suitable connection means able to leak-free connect the fluid receiving receptacle can also be used, such as thread engagement. The side-arm for vacuum connection has a zigzag shape and can also be other suitable shapes.

Figure 15B:
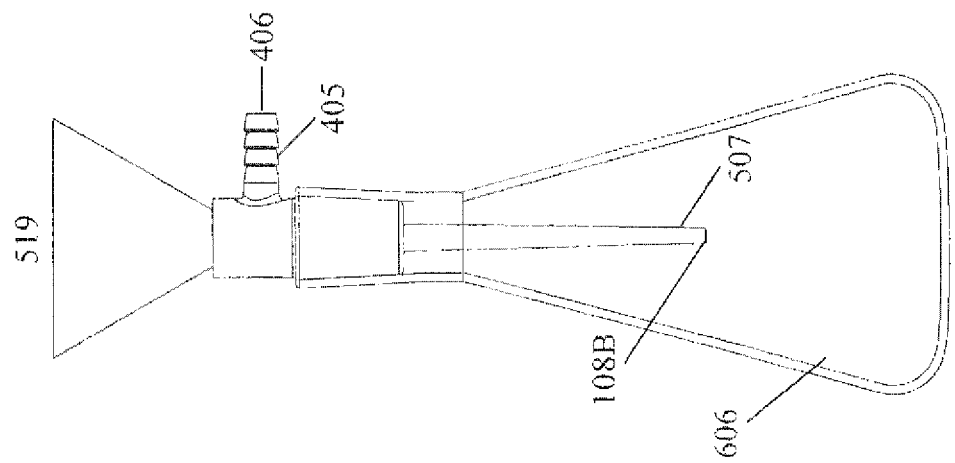
FIG. 15B is a connection diagram of the disposable integrated polymeric vacuum filtration funnel based on this invention fitting into a standard internally ground joint of the receiving Erlenmeyer flask, wherein the filtration funnel body having a conventional inverted cone shape, the seal adaptor having a externally ground joint, and the long outlet stem of the filtration funnel cut from pre-cut line to avoid close to the inner bottom of the receiving flask.
Figure 15A:
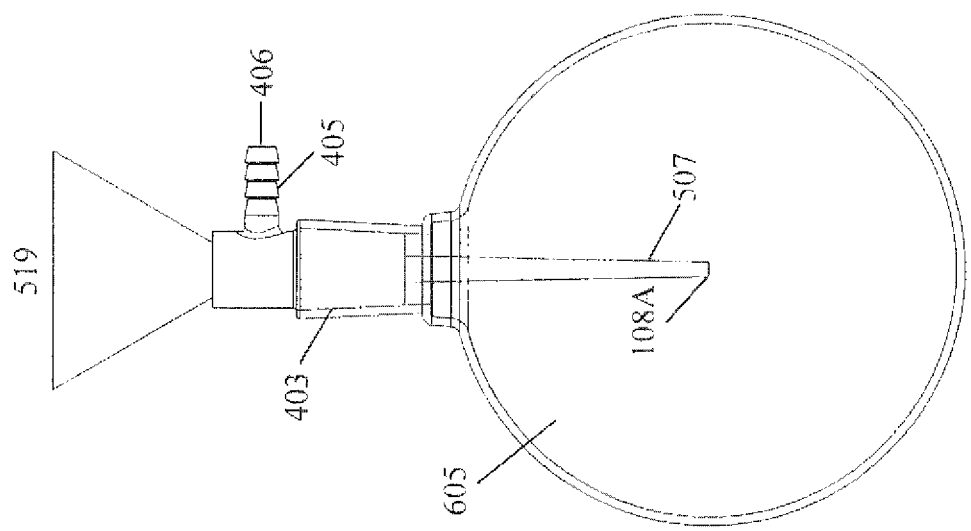
FIG. 15A is a connection diagram of the disposable integrated polymeric vacuum filtration funnel based on this invention fitting into a standard internally ground joint of the receiving flask, wherein the filtration funnel body having a conventional inverted cone shape, the seal adaptor having a externally ground joint, and the long outlet stem of the filtration funnel cut from pre-cut line to avoid close to the inner bottom of the receiving flask.

A typical flask is one of receiving receptacles and other suitable receiving receptacles having proper sealing joints can also be used, such as Erlenmeyer flasks 604 and 606 shown in FIGS. 14B and 15B. The outlet tip of the long outlet stem in this invention positions at much lower than side-arm, considerably reducing or completely eliminating the resultant sample loss being sucked away by vacuum. Meanwhile, the outlet tip of the long outlet stem toward near the bottom of the receiving receptacle can reduce or avoid fluid splashing and resultant sample damage. Since fluid splashing may not damage the filtered sample of small molecule mixture having a molecular mass less than 500 or 800, the outlet tips 107C, 107D, 108A, and 108B of long outlet stems 106 and 507 may be not required to be toward near the inner bottoms of round flasks 603 and 605, Erlenmeyer flasks 604 and 606 as shown in FIGS. 14A, 14B, 15A, and 15B but a considerably proper length is required to be away from the side-arm to avoid sample loss. The outlet stem can be partially cut to reduce length or connected with one or more extension tubes to extend length depending on the fluid material properties and the body depths of the receiving receptacles. Practically, the outlet stem 106 can be cut short to accommodate the shallow depth or height of the receiving receptacle. The use of plastic material to make outlet stem allows the ease of cutting. In an embodiment (not shown) of the present invention, the long outlet stem can be pre-cut annularly from outside toward inside for convenient application. The pre-cut depth is about a third of the wall thickness of the outlet steam but not more than two thirds to allow the end-user to easily break and save time. Considering the need for longer outlet stem of filtration funnel and the difficulty in production of long outlet stem of filtration funnel, in an embodiment (not shown) an outlet stem of filtration funnel in this invention can connect one or more extension tube of 80 mm to 200 mm or further longer extension tube to accommodate the deeper depth of receiving receptacle. The length of long outlet stem of filtration funnel can be easily cut short or lengthened with additional extension tubes; therefore it is very effective in application.

FIGS. 10A, 10B, 14A, 14B, 15A, 15B show only a single filtration setup comprising a single vacuum filtration funnel and a single receiving receptacle. In a case of three-necked flask with ground joints, one to three vacuum filtration funnels can be used to conduct multiple funnel filtering, speeding up the filtration operation. Similarly, increasing the number of ground joints of receiving receptacle can make multiple funnel filtering.

In addition, packing materials such as silica gel, C18 and other specialty reagents modified silica gel and resin can be packed into the integrated polymeric vacuum filtration funnels shown in FIGS. 10A, 10B, 14A, 14B, 15A, and 15B, so as to function as vacuum filtration separation columns for solid phase extraction. The packing material may also include, but not limited to, filtration aids and desiccants et al. Diatomaceous earth as filter aid can help solid-liquid separation. Desiccants such as anhydrous magnesium sulfate, sodium sulfate, and calcium sulfate are added to absorb water from the solid-liquid mixture then directly subjected to a vacuum filtration to remove drying agents and solid particles, simultaneously accomplishing both drying and filtering.

In this invention, the components of integrated polymeric vacuum filtration funnel and welding assembly are illustrated in FIGS. 1A-9B and 11A-13B. Although the funnel body components 100 and 500, and the sealing joint 400 having side-arm can be integrally produced, they are preferred made separately in this invention to allow a combination of different sizes of both funnel body components and sealing joints.

The components shown in FIGS. 1A-9B and 11A-13B in this invention can be made from the process of, including but not limited to, injection molding, extrusion molding, and thermal forming.

The present invention has been described in terms of specific preferred embodiments and implementations of the inventive concept, for purposes of illustration only. The scope of the invention should not be considered limited to the present embodiments and the specific form set forth herein. Any changes, modifications, and equivalent technical means for ordinary skill in the art according to the present inventive concepts should be considered as without departing from the spirit and scope of the invention.

What is claimed is:

1. A disposable vacuum filtration funnel for use with a vacuum comprising:
    a funnel body comprising a bottom wall; an annular step comprising an annular inner side surface extending vertically from said bottom wall; said annular step comprising a top surface extending horizontally from said annular inner side surface; and an annular inner sidewall extending vertically from said annular step; said bottom wall comprising an inner surface having an annular mounting portion; said funnel body comprising an outlet hole in said bottom wall;
    a filter comprising a bottom surface, an annular side surface, and a top surface; said bottom surface of said filter comprises an annular mounting portion sealed to said annular mounting portion of said inner surface of said bottom wall by a first weld; said annular side surface of said filter being sealed to said annular inner side surface of said annular step by a second weld; said top surface of said filter comprises an annular mounting portion;
    a press ring sealed to said annular mounting portion of said top surface of said filter by a third weld; said press ring is sealed to said top surface of said annular step by a fourth weld; said press ring is sealed to said inner sidewall of said funnel body by a fifth weld;
    an outlet stem sealed to said bottom wall of said funnel body and in fluid communication with said outlet hole; and
    whereby said first, second, third, fourth, and fifth welds form an absolute seal within said filtration funnel body allowing a high suction rate of the media thru said filter without loss of media around said filter.

2. The disposable vacuum filtration funnel of claim 1, wherein said outlet stem has a length in the range of 80 mm to 200 mm.

3. The disposable vacuum filtration funnel of claim 1, wherein said outlet stem and said funnel body are made from a single piece of material.

4. The disposable vacuum filtration funnel of claim 3, further comprising an adaptor sealed to said bottom wall of said funnel body; said adaptor comprises a side-arm configured to connect to the vacuum and an inlet in communication with said funnel body.

5. The disposable vacuum filtration funnel of claim 4, wherein said funnel body comprises an annular protrusion extending outward from said bottom wall and surrounding said opening of said funnel body; said annular protrusion of said funnel body extending into and being joined to said inlet of said adaptor by a sixth weld.

6. The disposable vacuum filtration funnel of claim 5, wherein said top surface of said filter extends above said top surface of said annular step.

7. The disposable vacuum filtration funnel of claim 1, wherein said press ring is of annular triangular shape.

8. The disposable vacuum filtration funnel of claim 1, wherein said first weld is an ultrasonic weld.

9. A disposable vacuum filtration funnel for use with a vacuum comprising:
    a funnel body comprising a bottom wall; a first annular step comprising a first annular inner side surface extending vertically from said bottom wall; said first annular step comprising a first top surface extending horizontally from said first annular inner side surface; a second annular step comprising a second annular inner side surface extending from said first top surface of said first annular step; said second annular step comprising a second tog surface extending horizontally from said second annular inner side surface; and an annular inner sidewall extending from said second top surface of said second annular step; said bottom wall comprising an inner surface having an annular mounting portion; said funnel body comprising an outlet hole in said bottom wall;
    a filter comprising a bottom surface, an annular side surface, and a top surface; said bottom surface of said filter comprises an annular mounting portion sealed to said annular mounting portion of said inner surface of said bottom wall by a first weld; said annular side surface of said filter being sealed to said first annular inner side surface by a second weld; said top surface of said filter comprises an annular mounting portion;
    a press ring sealed to said annular mounting portion of said top surface of said filter by a third weld; said press ring is sealed to said first top surface of said first annular step by a fourth weld; said press ring is sealed to said second annular inner side surface of said funnel body by a fifth weld;
    an outlet stem sealed to said bottom wall of said funnel body and in fluid communication with said outlet hole; and
    whereby said first, second, third, fourth, and fifth welds form an absolute seal within said filtration funnel body allowing a high suction rate of the media thru said filter without loss of media around said filter.

10. The disposable vacuum filtration funnel of claim 9, wherein said press ring further comprises an annular protrusion joined to said top surface of said filter by a sixth weld.

11. The disposable vacuum filtration funnel of claim 10, wherein said outlet stem has a length in the range of 80 mm to 200 mm.

12. The disposable vacuum filtration funnel of claim 11, wherein said outlet stem and said funnel body are made from a single piece of material.

13. The disposable vacuum filtration funnel of claim 12, further comprising an adaptor sealed to said bottom wall of said funnel body; said adaptor comprises a side-arm configured to connect to the vacuum and an inlet in communication with said funnel body.

14. The disposable vacuum filtration funnel of claim 13, wherein said funnel body comprises an annular protrusion extending outward from said bottom wall and surrounding said opening of said funnel body; said annular protrusion extending into and being joined to said inlet of said adaptor by a seventh weld.

15. The disposable vacuum filtration funnel of claim 14, wherein said top surface of said filter extends above said first top surface of said first annular step.

16. The disposable vacuum filtration funnel of claim 9, wherein said press ring is of annular triangular shape.

17. The disposable vacuum filtration funnel of claim 9, wherein said first weld is an ultrasonic weld.

* * * * *